United States Patent
Beebe et al.

(10) Patent No.: US 8,993,243 B2
(45) Date of Patent: Mar. 31, 2015

(54) METHOD FOR ISOLATING WEAKLY INTERACTING MOLECULES FROM A FLUIDIC SAMPLE

(75) Inventors: David Beebe, Monona, WI (US); Richard Burgess, Madison, WI (US); Lindsay Strotman, Madison, WI (US); Scott Berry, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 263 days.

(21) Appl. No.: 12/987,934

(22) Filed: Jan. 10, 2011

(65) Prior Publication Data

US 2012/0178096 A1 Jul. 12, 2012

(51) Int. Cl.
*C12Q 1/68* (2006.01)
*G01N 33/543* (2006.01)

(52) U.S. Cl.
CPC ........ *G01N 33/54326* (2013.01); *G01N 33/543* (2013.01)
USPC ........................... 435/6.19; 436/514; 436/518

(58) Field of Classification Search
None
See application file for complete search history.

(56) References Cited

U.S. PATENT DOCUMENTS

| | | | |
|---|---|---|---|
| 3,692,876 A * | 9/1972 | Ackermann et al. ........... | 525/133 |
| 4,504,588 A * | 3/1985 | Gartner et al. .................. | 502/24 |
| 4,645,747 A * | 2/1987 | Cais et al. ...................... | 436/500 |
| 5,139,933 A * | 8/1992 | Green et al. ................. | 435/7.32 |
| 5,279,936 A | 1/1994 | Vorpahl | |
| 5,695,990 A * | 12/1997 | Cubicciotti ................. | 435/317.1 |
| 5,876,924 A * | 3/1999 | Zhang et al. ...................... | 435/5 |
| 6,117,398 A | 9/2000 | Bienhaus et al. | |
| 8,017,340 B2 | 9/2011 | Collier et al. | |
| 8,048,633 B2 | 11/2011 | Collier et al. | |
| 8,304,188 B2 | 11/2012 | Kelso et al. | |
| 2006/0073533 A1* | 4/2006 | Pozueta Romero et al. . | 435/7.92 |
| 2009/0246782 A1 | 10/2009 | Kelso et al. | |
| 2010/0291666 A1 | 11/2010 | Collier et al. | |
| 2011/0223683 A1* | 9/2011 | Regnier et al. ................. | 436/501 |
| 2012/0094275 A1 | 4/2012 | Rao et al. | |

FOREIGN PATENT DOCUMENTS

| | | |
|---|---|---|
| WO | 2006071770 A2 | 7/2006 |
| WO | 2009111316 A2 | 7/2006 |
| WO | 2011098089 A1 | 8/2011 |

OTHER PUBLICATIONS

Sur (2010) J Mol Diag 12: 628-628.*
Atencia and Beebe, "Controlled Microfluidic Interfaces," Nature 437:648-655 (2005).
Zhao et al., "Surface-Directed Liquid Flow Inside Microchannels," Science 291:1023-1026 (2001).

(Continued)

*Primary Examiner* — Chris L Chin
*Assistant Examiner* — Richard Moerschell
(74) *Attorney, Agent, or Firm* — Armstrong Teasdale LLP

(57) ABSTRACT

Methods of isolating weakly interacting molecules in a fluidic sample using an immiscible phase filtration technique are disclosed. A complex is formed between a solid phase substrate, a molecule immobilized on the solid phase substrate, and at least one target molecule present in the fluidic sample. The complex is transferred into an immiscible phase by applying an external force to the solid phase substrate. The methods eliminate the need for complex and time consuming washing steps.

25 Claims, 11 Drawing Sheets

(56) References Cited

OTHER PUBLICATIONS

Shikida et al., "Using wettability and interfacial tension to handle droplets of magnetic beads in a micro-chemical-analysis system," Sensors and Actuators B113:563-569 (2006).

Okochi et al., "Droplet-based gene expression analysis using a device with magnetic force-based-droplet-handling system," J. Biosci. Bioeng. 109(2):193-197 (2010).

Tsuchiya et al., "On-chip polymerase chain reaction microdevice employing a magnetic droplet-manipulation system," Sensors and Actuators B130:583-588 (2008).

Shikida et al., "Development of an enzymatic reaction device using magnetic bead-cluster handling," J. Micromech. Microeng. 16:1875-1883 (2006).

Chen et al., "Microfluidic inverse phase ELISA via manipulation of magnetic beads," Microfluidics and Nanofluidics 10 (3):593-605 (2010) (DOI:10.1007/s10404-010-0692-2).

Third-Party Submission under 37 C.F.R. 1.99, dated Oct. 18, 2011.

Certified priority document U.S. Appl. No. 60/638,177 for PCT/US2005/046772, filed Dec. 23, 2004.

Berry et al., Purification of Cell Subpopulations Via Immiscible Filtration Assisted by Surface Tension (IFAST), Biomed Microdevices (2011) 13:1033-1042.

International Search Report and Written Opinion for PCT/US2011/067133 mailed Apr. 11, 2012.

* cited by examiner

SINGLE iFAST

DOUBLE iFAST

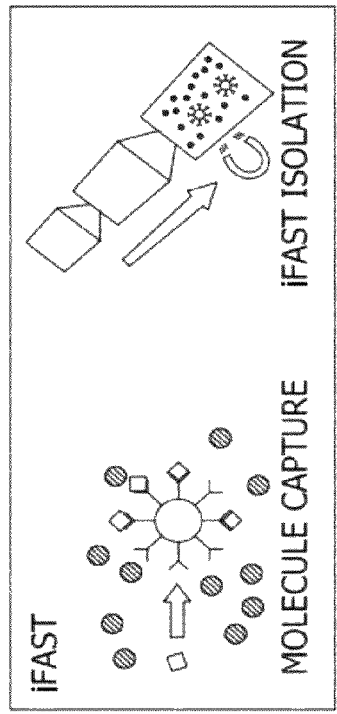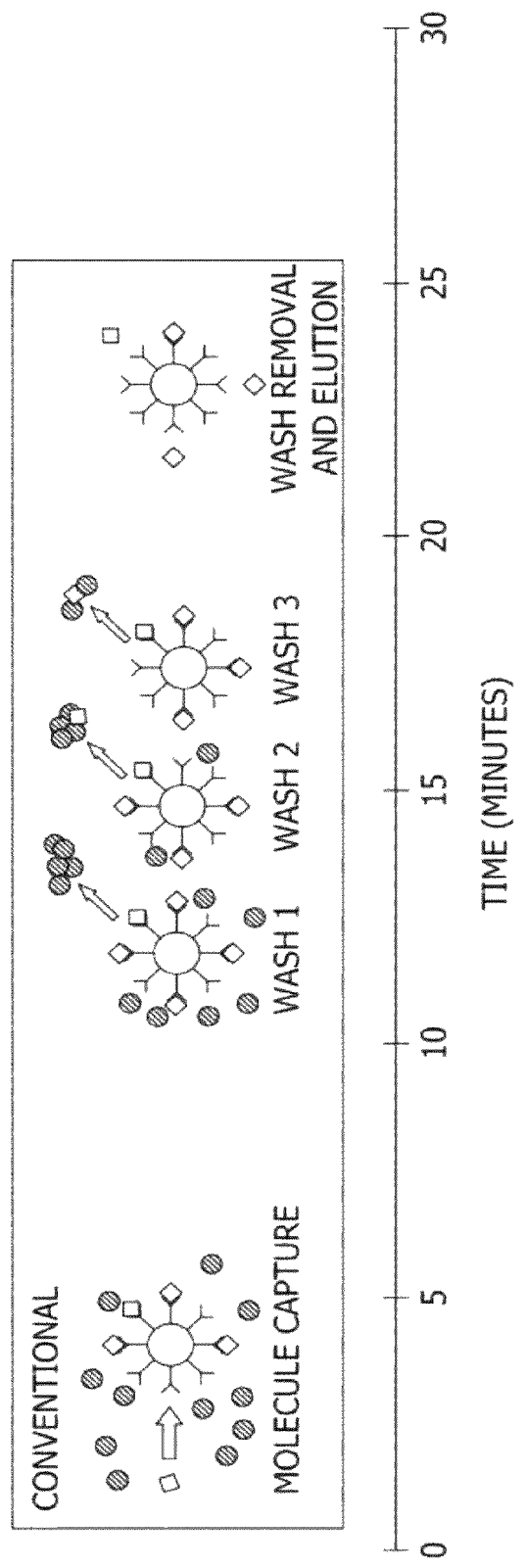

METHOD FOR ISOLATING WEAKLY INTERACTING MOLECULES FROM A FLUIDIC SAMPLE

STATEMENT REGARDING FEDERALLY SPONSORED RESEARCH OR DEVELOPMENT

This invention was made with government support under CA137673 awarded by the National Institutes of Health. The government has certain rights in the invention.

BACKGROUND OF THE DISCLOSURE

The present disclosure relates generally to methods for isolating molecules from a fluidic sample. More particularly, the present disclosure relates to methods for isolating weakly interacting molecules from a complex mixture using an immiscible phase filtration technique.

The isolation of proteins, nucleic acids, and small molecules from a complex biological mixture, such as a cell lysate or whole blood, is important in a broad array of fields, including biology, diagnostics, biochemistry, pharmacology, and forensics. In particular, molecule-molecule interactions such as, for example, protein-protein interactions, nucleic acid-nucleic acid interactions, protein-nucleic acid interactions, protein-small molecule interactions, and nucleic acid-small molecule interactions, among others, are important in a wide variety of cellular events. Because of the significance of molecule-molecule interactions, a number of physical, molecular biological, and genetic methods have been developed to isolate and identify molecular interactions.

Protein affinity chromatography, for example, uses a protein coupled to a matrix to isolate proteins that interact with the matrix-coupled protein. In this technique, non-interacting proteins are readily washed away under low-salt conditions, while the interacting proteins are retained on the matrix. Immunoprecipitation (IP) is another isolation technique that uses antibody (Ab)-bound scaffolds such as, for example, agarose beads or paramagnetic particles (PMPs), to selectively bind a protein of interest. As with affinity chromatography, after the antibody binds its antigen, a series of washing steps are performed to remove unbound protein, nucleic acids, and cell debris, as well as residual lysis buffer, which may impede downstream analyses such as mass spectroscopy (MS).

Multi-step solid phase extraction may be used to isolate and purify nucleic acids. Solid phase extraction involves binding nucleic acids to an immobilized solid phase. Bound nucleic acids are repeatedly washed to remove contaminants before they are eluted for downstream processing. High throughput versions of solid phase extraction process based on microtiter plate architectures are also commercially available, but these processes are labor intensive and can require expensive robotics to facilitate the extensive washing that must be performed on individual samples, which again limits widespread adoption of these techniques.

Recently, researchers have developed microfluidic embodiments of immunoprecipitation. However, such techniques typically require multiple washing steps which increase the complexity of microfluidic device design and operation, thus hindering the implementation of such platforms within non-engineering disciplines. Alternative techniques have been developed that rely on principles such as nano-sieving or partitioning into PEG-rich fluids using genetically-engineered tags, but these techniques possess a fair degree of microfluidic engineering complexity. While microfluidic embodiments can provide practical advantages (e.g. reduced reagent consumption, increased automation, lower device cost, and enhanced throughput), they have not offered significant improvements in the isolation of proteins or other molecules.

While the methods described above are suitable for isolating strongly interacting molecules, the required washing steps in these methods can inadvertently wash away weakly interacting molecules. Consequently, the isolation of weakly interacting molecules has been technically challenging. Accordingly, there exists a need to develop methods for isolating the wide variety of biologically important, but weakly interacting molecules.

BRIEF DESCRIPTION OF THE DISCLOSURE

The present disclosure is generally directed to methods for isolating weakly interacting molecules from a fluidic sample. More particularly, the present disclosure is directed to isolating weakly interacting molecules from a fluidic sample using an immiscible phase filtration technique.

In one aspect, the present disclosure is directed to a method for isolating weakly interacting molecules from a fluidic sample. The method comprises forming a mixture comprising the fluidic sample and a solid phase substrate, wherein the solid phase substrate comprises at least one immobilized molecule thereon; incubating the mixture under conditions sufficient for the immobilized molecule to interact with a target molecule in the fluidic sample to form a solid phase substrate-immobilized molecule-target molecule complex, wherein the immobilized molecule and the target molecule have an interaction half-life of about 10 minutes or less; and transferring the solid phase substrate-immobilized molecule-target molecule complex into an immiscible phase in about 1 second or less.

In another aspect, the present disclosure is directed to a method for isolating weakly interacting molecules from a fluidic sample comprising forming a mixture comprising the fluidic sample and a solid phase substrate, wherein the solid phase substrate comprises at least one immobilized molecule thereon; incubating the mixture under conditions sufficient for the immobilized molecule to interact with a target molecule in the fluidic sample to form a solid phase substrate-immobilized molecule-target molecule complex, wherein the immobilized molecule and the target molecule have an interaction half-life of about 5 seconds or less; and transferring the solid phase substrate-immobilized molecule-target molecule complex into an immiscible phase.

In yet another aspect, the present disclosure is directed to a method for isolating weakly interacting molecules from a fluidic sample comprising forming a mixture comprising the fluidic sample and a solid phase substrate, wherein the solid phase substrate comprises at least one immobilized molecule thereon; incubating the mixture under conditions sufficient for the immobilized molecule to interact with a target molecule in the fluidic sample to form a solid phase substrate-immobilized molecule-target molecule complex, wherein the target molecule interacts with at least one additional molecule in the fluidic sample, and wherein the target molecule and the at least one additional molecule have an interaction half-life of about 10 minutes or less; and transferring the solid phase substrate-immobilized molecule-target molecule complex into an immiscible phase in about 1 second or less.

In still another aspect, the present disclosure is directed to a method for isolating weakly interacting molecules from a fluidic sample comprising forming a mixture comprising the fluidic sample and a solid phase substrate, wherein the solid phase substrate comprises at least one immobilized molecule thereon; incubating the mixture under conditions sufficient for the immobilized molecule to interact with a target molecule in the fluidic sample to form a solid phase substrate-immobilized molecule-target molecule complex, wherein the target molecule interacts with at least one additional molecule in the fluidic sample, and wherein the target molecule and the at least one additional molecule have an interaction half-life of about 5 seconds or less; and transferring the solid phase substrate-immobilized molecule-target molecule complex into an immiscible phase.

In accordance with the present disclosure, methods have been discovered that surprisingly allow for the isolation and identification of weakly interacting molecules from a fluidic sample using immiscible phase filtration. The methods of the present disclosure have a broad and significant impact, as they allow interactions between molecules that were previously unidentifiable using traditional methods to be identified, and a "snapshot" of the molecular interactions at (or close to) equilibrium to be obtained. This is not possible with traditional methods that use aqueous wash steps, as equilibrium is perturbed with each wash step, which results in the loss of weakly interacting molecules.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1 is an isometric view of a device useful for isolating weakly interacting molecules from a complex mixture using an immiscible phase filtration technique.

FIG. 2 is a cross-sectional view of a device useful for isolating weakly interacting molecules from a complex mixture using an immiscible phase filtration technique taken along line 2-2 of FIG. 1.

FIG. 6A is an illustration of molecule capture and isolation using an iFAST device.

FIG. 6B is an illustration of molecule capture, wash steps, and wash removal and elution used in a conventional immunoprecipitation assay.

Figure 3A:
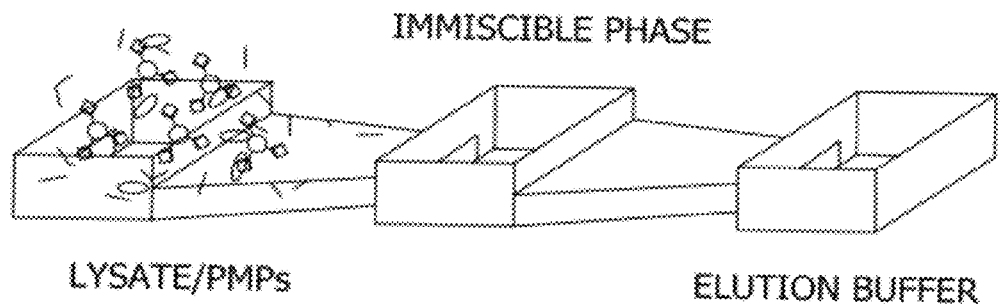
FIG. 3A is an illustration of a three well iFAST device showing lysate/PMP in the input zone.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, methods have been discovered that surprisingly allow for the isolation and identification of weakly interacting molecules from a fluidic sample using immiscible phase filtration. Advantageously, the methods of the present disclosure allow for rapid isolation of weakly interacting molecules from a fluidic sample, without the need for wash steps. Isolation of weakly interacting molecules is typically not possible with traditional methods that use aqueous wash steps, as equilibrium is perturbed with each wash step, which results in the loss of weakly interacting molecules. The rapid isolation of weakly interacting molecules achieved using the methods of the present disclosure opens up a range of experimental avenues not previously possible, including and related to enzyme kinetics, discovery of weakly bound co-regulators, and sensing of weakly bound analytes, as well as other weakly interacting molecules.

Molecule-Molecule Interactions

The methods of the present disclosure may be used to isolate and identify a number of molecule-molecule interactions. Non-limiting examples of such molecule-molecule interactions include a protein-protein interaction, a protein-protein complex interaction, a protein-small molecule interaction, a nucleic acid-nucleic acid interaction, a nucleic acid-small molecule interaction, a small molecule-small molecule interaction, a cell-protein interaction, a cell-nucleic acid interaction, a cell-small molecule interaction, and combinations thereof. Specific examples of molecule-molecule interactions may be antigen-antibody; carbohydrates-lectins; receptor-ligand; post-translational modifications such as, for example, carbohydrates, phosphorylated proteins, dephosphorylated proteins, and reversibly phosphorylated proteins; enzyme-cofactor; enzyme-substrate; enzyme-enzyme inhibitor, and the like.

Molecule-molecule interactions can be characterized based on the lifetime of their interaction. The terms "weakly interacting molecules," "transiently interacting molecules," or "weakly bound molecules," used interchangeably herein, refer to molecules that have a short interaction half-life. For purposes of the present disclosure, molecule-molecule interactions having an interaction half-life of about 10 minutes or less would be considered to be weakly interacting or transiently interacting. Weakly interacting or transiently interacting molecules are thus characterized by a tendency to associate and dissociate from one another, while strongly interacting molecules are very stable. The terms "strongly interacting molecules" or "tightly interacting molecules," used interchangeably herein, refer to molecules having longer interaction half-life. For purposes of the present disclosure, molecule-molecule interactions having an interaction half-life greater than 10 minutes would be considered to be strongly interacting.

The strength of a molecule-molecule interaction may also be described by the equilibrium dissociation constant ($K_d$), which is equal to $k_{off}/k_{on}$, where $k_{off}$ is the rate constant of the molecule-molecule dissociation reaction and $k_{on}$ is the rate constant of the association reaction. For typical protein-protein interactions a $K_d$ of 1 nM would be expected to have a dissociation half-life of about 30 minutes, and thus, would be considered a strong or tight interaction. A $K_d$ of 10 nM would be expected to have a dissociation half-life of about 3 minutes, and thus, would be considered a weak or transient interaction. A $K_d$ of 100 nM would be expected to have a dissociation half-life of about 20 seconds, and thus, would be considered a weak or transient interaction. A $K_d$ of 1 mM would be expected to have a dissociation half-life of about 2 seconds, and thus, would be considered a weak or transient interaction.

For a strong protein-protein interaction (for example, antibody-antigen or protease-protease inhibitor) the $K_d$ is typically less than $10^{-12}$ to $10^{-9}$ M, which yields a half-life of about 12 minutes to 19 hours. For a weak protein-protein interaction (for example, phospho-transfer for protein kinases and phosphatases) $K_d$ is typically greater than $10^{-9}$ M, which yields a half-life of about 10 minutes or less.

Nucleic acid-nucleic acid interactions may be strong or weak depending on the degree of complementarity of each nucleic acid strand. This is of particular importance in detection methods that depend upon binding between nucleic acids. As used herein, "complementary" or "complementarity" are used according to their ordinary meaning as understood by one skilled in the art to refer to polynucleotides (i.e., a sequence of nucleotides such as an oligonucleotide or a target nucleic acid) related by the base-pairing rules. Complementarity may be "partial," in which only some of the nucleic acids bases match according to the base pairing rules or there may be "complete" complementarity between the nucleic acids.

Nucleic acid-nucleic acid interactions may also be strong or weak depending on the stringency of the fluidic sample. As used herein, "stringency" is used according to its ordinary meaning as understood by one skilled in the art to refer to reaction conditions such as temperature, salt concentration(s), and pH that dictate the annealing or hybridization of nucleic acid-nucleic acid interactions such as, for example, DNA-DNA, DNA-RNA and RNA-RNA. For example, at high stringency, nucleic acid-nucleic acid interactions (i.e., annealing) form only between strands with perfect one to one complementarity. Lower stringency allows interactions between nucleic acid strands with some degree of mismatch between bases. By varying the conditions such as salt concentration and temperature a given nucleic acid may hybridize only with its exact complement (high stringency), or with any somewhat related sequences (low or weak stringency). Increasing the temperature or decreasing the salt concentration will tend to increase the selectivity of a hybridization reaction, and thus increases the stringency. Thus, conditions of "weak" or "low" stringency are often required when it is desired to hybridize or anneal nucleic acids which are not completely complementary to one another.

While the methods of the present disclosure may be used to isolate and identify some interactions having a long interaction half-life, advantageously, the method also allows for the isolation of weakly interacting molecules.

Immiscible Phase Filtration

The methods of the present disclosure use an immiscible phase filtration technique to isolate and identify weakly interacting molecules. In general, the methods of the present disclosure involve mixing a fluidic sample with a solid phase substrate that has at least one molecule (e.g., antibody, nucleic acid, and/or any other molecule of interest) immobilized thereon. The mixture is incubated for a sufficient period of time to allow the immobilized molecule to interact with molecules in the fluidic sample. An external force is then used to transfer the solid phase substrate, and thus the immobilized molecule and any molecules associated with (e.g., molecules bound to or complexed with) the immobilized molecule, into an immiscible phase. Molecules associated with the immobilized molecule are thus separated from any unassociated or unbound components, which are unlikely to pass into the immiscible phase without the aid of the solid phase substrate, and consequently remain in the fluidic sample. In some embodiments, the solid phase substrate, immobilized molecule, and molecules associated with the immobilized molecule, are transferred through the immiscible phase and into a solution (e.g., elution buffer). Because the methods of the present disclosure allow weakly interacting molecules to rapidly be separated from unassociated contaminants without the need for a wash step, weak interactions between molecules that were previously unidentifiable using traditional methods can be identified, and a "snapshot" of the molecular interactions at (or close to) equilibrium can be obtained.

Thus, in one aspect, the present disclosure is directed to a method for isolating weakly interacting molecules from a fluidic sample. The method comprises forming a mixture comprising a fluidic sample and a solid phase substrate, wherein the solid phase substrate comprises at least one immobilized molecule thereon, incubating the mixture under conditions sufficient for the immobilized molecule to interact with a target molecule in the fluidic sample to form a solid phase substrate-immobilized molecule-target molecule complex, and transferring the solid phase substrate-immobilized molecule-target molecule complex into an immiscible phase. The complex may be transferred into the immiscible phase by application of an external force to the solid phase substrate, as described elsewhere herein. In one embodiment, the immobilized molecule and the target molecule are weakly interacting molecules, and have an interaction half-life of about 10 minutes or less. In some such embodiments, the target molecule may also further interact with at least one additional molecule in the fluidic sample. For instance, the target molecule may be part of a larger complex comprising the at least one additional molecule. In such embodiments, the interaction between the target molecule and the at least one additional molecule may be strong (e.g., the molecules have an interaction half-life of greater than 10 minutes) or may be weak (e.g., the molecules have an interaction half-life of about 10 minutes or less).

In other embodiments, the immobilized molecule and the target molecule are strongly interacting molecules, and have an interaction half-life of greater than 10 minutes. In such embodiments, the target molecule will preferably also interact with at least one additional molecule in the fluidic sample. For instance, the target molecule may be part of a larger complex comprising at least one additional molecule. In such embodiments, the interaction between the target molecule and the at least one additional molecule is weak (e.g., the molecules have an interaction half-life of about 10 minutes or less).

In some embodiments, the immobilized molecule and the target molecule (or the target molecule and the at least one additional molecule) may have an interaction half-life of about 5 minutes or less. In yet another embodiment, the interaction half-life is about 1 minute or less. In still another embodiment, the interaction half-life is about 30 seconds or less. In yet another embodiment, the interaction half-life is about 5 seconds or less. In another embodiment, the interaction half-life is about 2 seconds or less.

Immobilizing at least one molecule on the solid phase substrate is typically performed prior to forming the mixture. The mixture of the fluidic sample and the solid phase substrate having at least one immobilized molecule is incubated under conditions sufficient for the immobilized molecule to interact with a target molecule. Suitable incubations conditions may vary, and will depend on a variety of factors, including the composition of the fluidic sample, the immobilized molecule, the target molecule, the relative concentration of the immobilized molecule, the relative concentration of the target molecule and/or molecules associated therewith, temperature, pH, ionic strength of the sample, mixing or agitation (e.g., presence or absence of convection), and combinations thereof. Preferably, the mixture is incubated until an equilibrium between the immobilized molecule and the target molecule is achieved. Suitable incubation times may vary and can be readily determined by one skilled in the art, but typically will range from less than about one minute to about 24 hours or more.

The solid phase substrate-immobilized molecule-target molecule complex (including any additional molecules associated with the target molecule) may be rapidly transferred into the immiscible phase. The transfer time of the complex from the mixture into the immiscible phase is typically about 1 second or less, including about 100 milliseconds or less, about 50 milliseconds or less, about 20 milliseconds or less, and about 10 milliseconds or less, and further including from about 10 milliseconds to about 1 second. The time it takes to transfer the complex from the mixture into the immiscible phase is measured starting from the time the complex first contacts the immiscible phase and begins to exit the mixture, and ending at the time the complex is completely within the immiscible phase.

In some embodiments, once in the immiscible phase, the solid phase substrate-immobilized molecule-target molecule complex (including any additional molecules associated with the target molecule) may be eluted and/or subjected to further downstream processing, as described elsewhere herein, directly from the immiscible phase.

In other embodiments, the solid phase substrate-immobilized molecule-target molecule complex (including any additional molecules associated with the target molecule) is transferred through the immiscible phase and into a solution (e.g., elution buffer, detection reagent, downstream processing reagent, etc., and combinations thereof). Once in the solution, the target molecule (including any additional molecules associated with the target molecule) may be eluted and/or subjected to further downstream processing. The complex may be transferred into the solution by application of an external force to the solid phase substrate, as described elsewhere herein. Thus, transfer of the solid phase substrate-immobilized molecule-target molecule complex (including any additional molecules associated with the target molecule) may terminate in either the immiscible phase or in a separate solution.

In some embodiments, once the solid phase substrate-immobilized molecule-target molecule complex (including any additional molecules associated with the target molecule) is transferred into the immiscible phase, the complex may be incubated and/or processed (e.g., contacted with detection and/or other processing reagents) in the immiscible phase before being further transferred through the immiscible phase and into the solution. In these embodiments, suitable incubation times will vary depending on a variety of factors. Considerations in determining suitable incubation times in the immiscible phase include the degree of adsorption of the solid phase substrate-immobilized molecule-target molecule complex (including any additional molecules associated with the target molecule) or solid phase substrate-immobilized molecule onto the wall of the device in which the immiscible phase transfer is being performed; absorption of the solid phase substrate; immobilized molecule; and/or target molecule (including any additional molecules associated with the target molecule) into the immiscible phase; the need to remove hydrophobic and/or lipophilic material associated with the complex; the need to increase molecular interactions; and the desire to perform downstream processing (e.g., protein crystallization); among others. In some embodiments, suitable incubation time in the immiscible phase may be up to several hours or more.

In other embodiments, the solid phase substrate-immobilized molecule-target molecule complex may be transferred from the mixture through the immiscible phase and into the solution without extended incubation and/or processing in the immiscible phase. For instance, in some embodiments, the solid phase substrate-immobilized molecule-target molecule complex may be transferred from the mixture through the immiscible phase and into the solution very rapidly, for example, in about 10 seconds or less. In other embodiments, the solid phase substrate-immobilized molecule-target molecule complex is transferred from the mixture through the immiscible phase and into the solution in about 5 seconds or less. In yet another embodiment, the solid phase substrate-immobilized molecule-target molecule complex is transferred from the mixture through the immiscible phase and into the solution in about 100 milliseconds or less. In another embodiment, the solid phase substrate-immobilized molecule-target molecule complex is transferred from the mixture through the immiscible phase and into the solution in from about 100 milliseconds to about 10 seconds. The transfer time of the complex from the mixture through the immiscible phase and into the solution is measured starting from the time the complex first contacts the immiscible phase and begins to exit the mixture, and ending at the time the complex is completely within the solution. It has been surprisingly discovered that rapidly transferring the solid phase substrate-immobilized molecule-target molecule complex from the mixture through the immiscible phase and into the solution allows for isolating weakly interacting molecules exhibiting half-lives of about 10 minutes or less.

As discussed herein, the solid phase substrate-immobilized molecule-target molecule complex may be transferred into the immiscible phase and/or into the solution by application of an external force to the solid phase substrate. In some embodiments, the external force is applied to the solid phase substrate for a period of time (e.g., a few seconds) before the transfer such that the solid phase substrate will be more responsive to movements of the external force. For instance, in embodiments where the solid phase substrate is responsive to a magnetic force, a magnet may be placed near the solid phase substrate in order to collect all of the solid phase substrate within the magnetic field, so that the solid phase substrate will be more responsive to movements of the magnet. In other embodiments, the external force is applied to initiate the transfer without a delay.

In some embodiments, the solid phase substrate-immobilized molecule-target molecule complex may be subjected to a further immiscible phase filtration step, by transferring the complex from the solution through a second immiscible phase, and into a second solution. This second filtration step may be used to further purify the target molecule or molecules associated therewith from any contamination or impurities that may unintentionally be carried over from the fluidic sample during transfer of the complex. For instance, in some embodiments where the solid phase substrate comprises a plurality of particles, the particles may aggregate when they are transferred from the mixture into the immiscible phase (or from the mixture through the immiscible phase and into the solution). In such embodiments, impurities from the fluidic sample may be trapped within the interstitial spaces of the aggregate, and carried over into the solution along with the solid phase substrate-immobilized molecule-target molecule complex. By transferring the solid phase substrate-immobilized molecule-target molecule complex from the first solution through a second immiscible phase, and into a second solution, some of these contaminants are left in the first solution.

The solid phase substrate-immobilized molecule-target molecule complex may be transferred from the mixture and into the second solution (i.e., including through both immiscible phases and the first solution) very rapidly, for example, in about 10 seconds or less, including about 5 seconds or less, and about 100 milliseconds or less, and further including from about 100 milliseconds to about 10 seconds. Without wishing to be bound to any particular theory, it is believed that because the solid phase substrate-immobilized molecule-target molecule complex is present in the first solution for such a short period of time, there is little to no dissociation of the target molecule (or any additional molecules associated with the target molecule) from the complex, and thus very few or none of the weakly interacting molecules are left behind in the first solution.

If desired, the solid phase substrate-immobilized molecule-target molecule complex may optionally be subjected to further immiscible phase filtration steps, for example, by transferring the complex from the second solution through a third, fourth, fifth, or more immiscible phase, and into additional solutions.

Fluidic Samples

The methods of the present disclosure may be used to isolate and/or identify weakly interacting molecules from a variety of samples. Suitable fluidic samples that may be used in the methods of the present disclosure include clinical samples such as, for example, blood, serum, sputum, saliva, tissue fluids, and urine, among others. Additional fluidic samples that may be used in the method of the present disclosure also include cell suspensions, cell culture media, cell mixtures, cell lysates, cell extracts, and combinations thereof. Cell mixtures or cell suspensions may be, for example, cell cultures, cell homogenates, a bacteria-containing sample, a multicellular organism-containing sample, and other cell-containing mixtures and suspensions, and combinations thereof. The fluidic sample may also be, for example, a cell-free mixture such as, for example, a protein-containing sample, a polypeptide containing sample, a peptide containing sample, a nucleic acid-containing sample, an oligonucleotide-containing sample, a nucleotide-containing sample, a small molecule-containing sample, and combinations thereof.

Solid Phase Substrates

Suitable solid phase substrates for use in the methods of the present disclosure are generally known in the art. Suitable solid phase substrates are responsive to an external force such as, for example, a magnetic field, gravitational force, centrifugal force, inertial force, mechanical force, physical force, pumping, and combinations thereof. Examples of suitable solid phase substrates include a particle, a membrane, a rod, a wire, a porous material such as a porous particle, and combinations thereof. Suitable particles may be, for example, microparticles, nanoparticles, magnetic particles, non-magnetic particles, non-porous particles such as non-porous beads, porous particles such as porous beads, and combinations thereof. Suitable magnetic particles may be, for example, paramagnetic particles, superparamagnetic particles, ferromagnetic particles, and combinations thereof.

As discussed herein, the solid phase substrate-immobilized molecule-target molecule complex may be transferred into the immiscible phase and/or through the immiscible phase and into the solution by application of an external force to the solid phase substrate. For example, in one embodiment, the solid phase substrate is a magnetic substrate (e.g., magnetic particles), and a magnetic force is applied to the solid phase substrate, and used to transfer the solid phase substrate-immobilized molecule-target molecule complex into the immiscible phase and/or through the immiscible phase and into the solution. Other embodiments may apply mechanical or physical force to a solid phase substrate, such as a rod or a wire. For example, a section of a rod or a section of a wire may be pushed or pulled in a manner that results in transfer of the section of rod or the section of wire from the mixture and into the immiscible phase or through the immiscible phase and into the solution. Other exemplary means of transfer are described in more detail elsewhere herein.

Immobilized and Target Molecules

As discussed herein, the methods of the present disclosure may be used to isolate and identify a number of molecule-molecule interactions, non-limiting examples of which include a protein-protein interaction, a protein-protein complex interaction, a protein-small molecule interaction, a protein-nucleic acid interaction, nucleic acid-nucleic acid interaction, a nucleic acid-small molecule interaction, a small molecule-small molecule interaction, a cell-protein interaction, a cell-nucleic acid interaction, a cell-small molecule interaction, a cell-protein complex interaction, and combinations thereof. Such interactions may be between the immobilized molecule and the target molecule and/or between the target molecule and at least one additional molecule present in the fluidic sample.

As used herein, the terms "immobilized" and "immobilizing" refer to attaching or linking a molecule to the solid phase substrate. The immobilized molecule may be, for example, a protein, a nucleic acid, a small molecule, a cell, and combinations thereof. Suitable proteins may be, for example, an antibody, a polypeptide, a peptide, and combinations thereof.

As used herein, "nucleic acid" refers to any nucleic acid containing molecule such as for example, DNA and RNA. A "small molecule" is used according to its ordinary meaning as understood by one skilled in the art to refer to a low molecular weight compound. Typically, small molecule compounds have molecular weights of about 100-1500 Daltons. Although some small molecules may interact with high affinity to a molecule, the method of the present disclosure can also be used to isolate molecules that weakly interact with the small molecule, and to isolate small molecules that weakly interact with other molecules, such as proteins, nucleic acids, and the like. Suitable small molecules may be, for example, small molecule drugs such as, for example, chemotherapeutic drugs, as well as adenosine triphosphate (ATP), nicotinamide adenine dinucleotide ($NAD^+$), a cofactor, a coenzyme, a prosthetic group, flavin, a metal ion, iron, magnesium, manganese, nickel, cobalt, copper, zinc, selenium, molybdenum, a vitamin, an iron-sulfur cluster, heme, and a metabolic substrate or an analog thereof, among others. Additionally, small molecules include molecules of a combinatorial library of compounds that share a chemical structure.

Various combinations of immobilized molecules may also be used. For example, the molecules immobilized onto the solid phase substrate may be the same molecule (e.g., a single protein), the same type of molecule (e.g., two or more types of antibodies, such as monoclonal and polyclonal antibodies), or alternately may be different types of molecules entirely (e.g., a peptide and a small molecule). In one particular non-limiting example, antibodies against two different target molecules may be immobilized on the same solid phase substrate. In another embodiment a cell may be immobilized on the solid phase substrate.

Immobilizing the molecule to the solid phase substrate may be carried out using methods or techniques generally known in the art. Many kits available from commercial vendors (for example, Dynabeads from Invitrogen) are also suitable for this purpose. In some embodiments, the molecule is immobilized by directly or indirectly attaching the molecule to the solid phase substrate. Conjugation chemistry, for example, is a suitable process for directly immobilizing molecules to the solid phase substrate. Non-covalent binding, such as the binding of biotin to avidins, is a suitable indirect method for attaching the immobilized molecule to the solid phase substrate.

Another suitable indirect method of linking or attaching a molecule, such as antibodies, to the solid phase support involves use of a spacer molecule. A spacer molecule provides additional distance or separation between the solid phase substrate and immobilized molecule, for example, to limit possible steric hindrance that may otherwise interfere with immobilized molecule-target molecule (e.g., antibody-antigen) interaction. Suitable peptide spacer molecules may be, for example, chemical spacers, amino acid spacers, peptide spacers, and combinations thereof.

The target molecule may be any molecule in the fluidic sample that interacts, either weakly or strongly, with the immobilized molecule. As discussed herein, in one embodiment, the target molecule weakly interacts with the immobilized molecule. In some such embodiments, the target molecule may also interact with (e.g., be complexed with) at least one additional molecule. In this embodiment, the target molecule and the at least one additional molecule may interact strongly or weakly. In another embodiment, the target molecule strongly interacts with the immobilized molecule. In such embodiments, the target molecule will preferably also weakly interact with (e.g., be complexed with) at least one additional molecule.

The target molecule may be, for example, a cell, a cell complexed with at least one additional molecule, a protein, a protein complexed with at least one additional molecule, a nucleic acid (e.g., a DNA, a RNA), a nucleic acid complexed with at least one additional molecule, a small molecule, a small molecule complexed with at least one additional molecule, or some combination thereof. In embodiments where the target molecule interacts with at least one additional molecule, the additional molecule may also be, for example, a protein, a protein complexed with at least one additional molecule, a nucleic acid (e.g., a DNA or a RNA), a small molecule, a small molecule complexed with at least one additional molecule, a cell, and combinations thereof.

Immiscible Phase

To isolate weakly interacting molecules according to the method of the present disclosure, the solid phase substrate-immobilized molecule-target molecule complex is transferred into or through at least one immiscible phase. As used herein, "immiscible" refers to two fluid materials that, when positioned in contact with one another, form an interface which possesses phases of differing compositions on each side of the interface. The interfacial energy between the mixture and the immiscible phase and the immiscible phase and the solution is typically from about 0.2 mN/m to about 30 mN/m. The "strength" of the immiscible phase barrier between the mixture and the solution relies upon an interfacial energy between the mixture and the immiscible phase and between the immiscible phase and the solution. Reduction of the interfacial energy will result in the formation of a continuous aqueous phase or emulsion connecting the mixture and the solution, resulting in the mixing of the mixture and the solution. Excessively high interfacial energies may be too rigid to allow transfer into the immiscible phase.

Suitable materials that may be used to form the immiscible phase include, for example, an organic solvent, a liquid wax, an oil, a gas, and combinations thereof. Particularly suitable materials may be, for example, olive oil, mineral oil, silicone oil, chill-out liquid wax, paraffin wax (various melting points), and fluorinated oil.

In other embodiments, suitable waxes may be, for example, Chill-Out 14 wax (MJ Research), paraffin waxes such as IGI 1070A, microcrystalline waxes such as IGI Micosere 5788A, soy and palm waxes, for example, IGI R2322A, candle waxes, for example, IGI 6036A, thermoset waxes, for example, IGI Astorstat 75, hot melt adhesives, atactic polypropylene and polyolefin compounds, petroleum waxes, and dental waxes. Other suitable waxes may be, for example, waxes such as animal waxes (for example, beeswax, lanolin, and tallow), vegetable waxes (for example, carnauba, candelilla, and soy), mineral waxes, for example, fossil or earth (for example, ceresin or montan), and petroleum (for example, paraffin or microcrystalline) waxes. Still other suitable waxes may be, for example, synthetic (man-made) waxes for example, ethylenic polymers (for example, polyethylene or polyol ether-esters), chlorinated naphthalenes or hydrocarbon type waxes (for example, Fischer-Tropsch).

Suitable oils may be, for example, mineral oil, paraffin oil, silicon oil, fluorosilicone, fluorocarbon oil (for example, Fluorinert FC-40 from 3M), perfluorocarbon fluids (for example, Flutec Fluids from F2Chemicals), perfluorodecalin (for example, P9900 from Aldrich, Flutec PP6, FluoroMed APF-140HP), perfluoroperhydrophenanthrene (for example, FluoroMed APF-215M), perfluorooctylbromide (for example, FluoroMed APF-PFOB), and combinations thereof.

Other suitable immiscible phase materials may be, for example, organic solvents such as 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, and tetramethylene sulfone; ionic liquids (for example, BMIM[PF6], BMIM[Tf2N] and OMA[Tf2N] where: BMIM-bis(trifluoromethanesulfonyl)imide, PF6=1-n-butyl-3-methylimidazolium hexafluorophosphate, TfN2=bis(trifluoromethylsulfonyl)imide, and OMA=methyltrioctylammonium); 1-Butyl-3-methylimidazolium tetrafluoroborate ECOENG™ 21M, 1-Ethyl-3-hydroxymethylpyridinium ethylsulfate, Butylmethylpyrrolidinium bis(trifluoromethylsulfonyl)imide, ECOENG™ 212, ECOENG™ 1111P (all available from Solvent Innovations), and combinations thereof.

Elution and Downstream Processing

Suitable methods for eluting or removing the target molecule (including any additional molecules associated with the target molecule) from the immobilized molecule are known to those skilled in the art. In some embodiments, the immobilized molecule may also be eluted or removed from the solid phase substrate. In other embodiments, the immobilized molecule is eluted from the solid phase substrate and the target molecule (including any additional molecule associated with the target molecule) is eluted from the immobilized molecule. Suitable elution methods known to those skilled in the art may be, for example, ionic strength; pH; temperature; competitor molecules; inhibitor molecules; restriction enzymes; proteases; detergent-based elution, and combinations thereof.

Suitable downstream processing methods are known to those skilled in the art and may be, for example, detection methods such as, for example, mass spectrometry, fluorescence, radioimmunoassay, and chemiluminescence; electrophoresis methods such as, for example, polyacrylamide gel electrophoresis, Western blot, ELISA; enzyme assays; amplification such as, for example, polymerase chain reaction (PCR); reverse transcription (e.g., of RNA); hybridization such as, for example, in situ hybridization, Northern blot analysis, Southern blot analysis, labeled probe hybridization; sequencing; chemical cross-linking; protein crystallization; and combinations thereof.

Devices

Figures 1, 2:
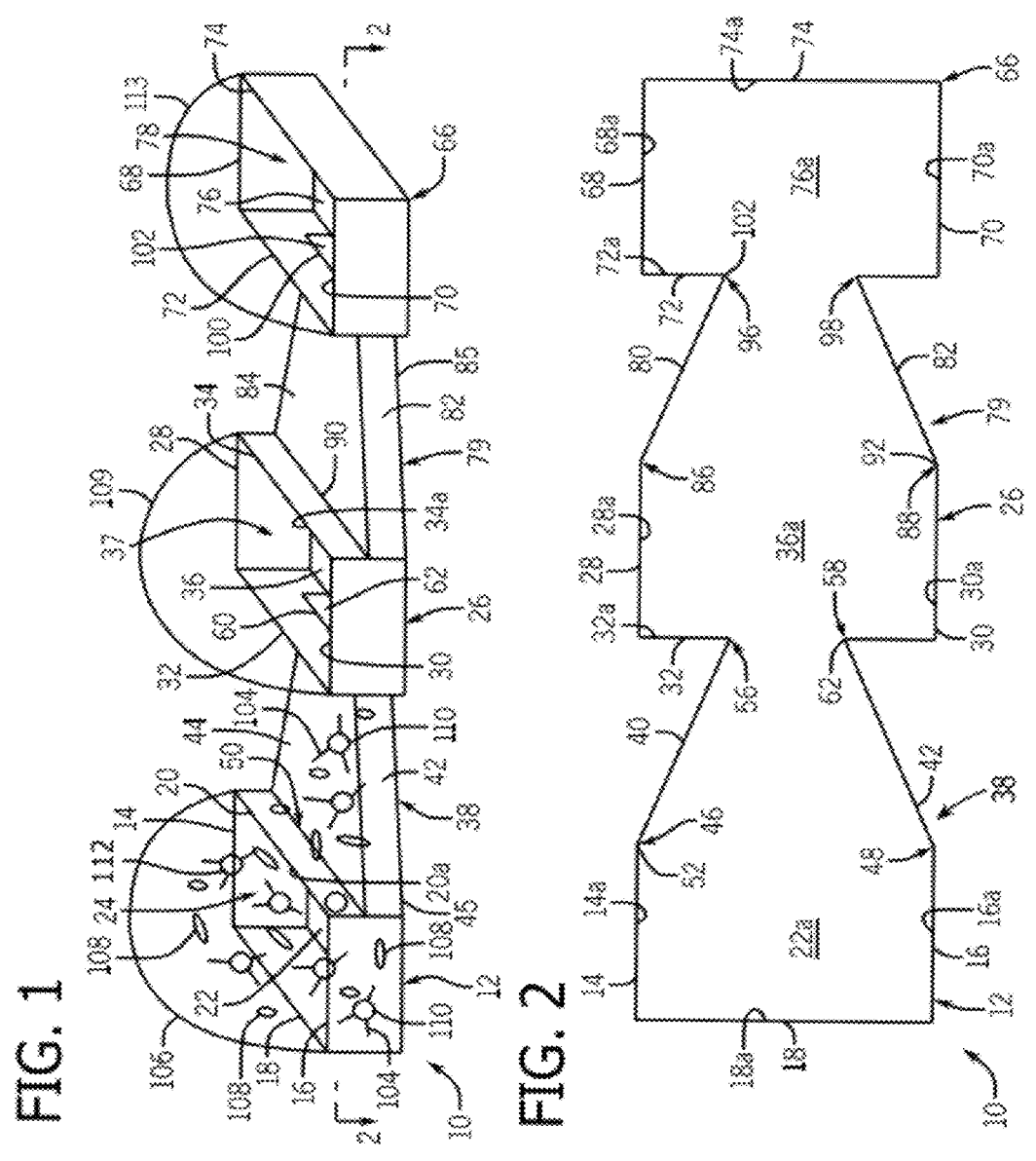

Referring to FIGS. 1 and 2, a device for effectuating the methods of isolating weakly interacting molecules using immiscible phase filtration according to the present disclosure is generally designated by the reference numeral 10. Device 10, also referred to herein as an immiscible filtration assisted by surface tension ("iFAST") device, includes input zone (used interchangeably herein with the term "input well") 12 defined by first and second sidewalls 14 and 16, respectively, first and second end walls 18 and 20, respectively, and bottom wall 22. Inner surfaces 14a and 16a of sidewalls 14 and 16, respectively, inner surfaces 18a and 20a of first and second end walls 18 and 20, respectively, and upper surface 22a of bottom wall 22 define input cavity 24 for receiving a fluidic sample therein, as hereinafter described. While input well 12 has a generally rectangular configuration in the depicted embodiment, other configurations are contemplated without deviating from the scope of the present disclosure.

Device 10 further includes immiscible phase zone (used interchangeably herein with the term "immiscible phase well") 26 downstream of input well 12 and being defined by first and second sidewalls 28 and 30, respectively, upstream wall 32, downstream wall 34 and bottom wall 36. Inner surfaces 28a and 30a of sidewalls 28 and 30, respectively, inner surface 32a of upstream wall 32, inner surface 34a of downstream wall 34, and upper surface 36a of bottom wall 36 define immiscible phase cavity 37 for receiving an immiscible phase therein, as hereinafter described. Again, although immiscible phase well 26 has a generally rectangular configuration in the depicted embodiment, other configurations are contemplated without deviating from the scope of the present invention.

Input well 12 and immiscible phase well 26 are interconnected by first channel 38. First channel 38 extends along an axis and is defined by first and second sidewalls 40 and 42, respectively, upper wall 44 and bottom wall 45. Input ends 46 and 48 of first and second sidewalls 40 and 42, respectively, of first channel 38 and input end 50 of upper wall 44 of input channel 38 intersect end wall 20 of input well 12 so as to define input 52 to first channel 38. Output ends 56 and 58 of first and second sidewalls 40 and 42, respectively, of first channel 38 and output end 60 of upper wall 44 of first channel 38 intersect upstream wall 32 of immiscible phase well 26 so as to define output (also referred to herein as a "constriction") 62 of first channel 38. Bottom wall 45 of first channel 38 is generally co-planar with bottom walls 22 and 36 of input well 12 and immiscible phase well 26, respectively. As best seen in FIG. 2, first and second sidewalls 40 and 42, respectively, of first channel 38 constrict towards each other from input 52 to output 62, for reasons hereinafter described. Upper wall 44 and bottom wall 45 of first channel 38 may also constrict towards each other, for reasons hereinafter described.

Device 10 further includes output zone (used interchangeably herein with the term "output well") 66 downstream of immiscible phase well 26 and being defined by first and second sidewalls 68 and 70, respectively, upstream wall 72, downstream wall 74 and bottom wall 76. Inner surfaces 68a and 70a of sidewalls 68 and 70, respectively, inner surface 72a of upstream wall 72, inner surface 74a of downstream wall 74, and upper surface 76a of bottom wall 76 define output cavity 78 for receiving a solution therein, as hereinafter described. Again, output well 66 has a generally rectangular configuration in the depicted embodiment, other configurations are contemplated without deviating from the scope of the present invention.

Output well 66 and immiscible phase well 26 are interconnected by second channel 79. Second channel 79 extends along an axis and is defined by first and second sidewalls 80 and 82, respectively, upper wall 84 and bottom wall 85. Input ends 86 and 88 of first and second sidewalls 80 and 82, respectively, of second channel 79 and input end 90 of upper wall 84 of second channel 79 intersect downstream wall 34 of immiscible phase well 26 so as to define input 92 to second channel 79. Output ends 96 and 98 of first and second sidewalls 80 and 82, respectively, of second channel 79 and output end 100 of upper wall 84 of second channel 79 intersect upstream wall 72 of output well 66 so as to define output (also referred to herein as "constriction") 102 of second channel 79. Bottom wall 85 of second channel 79 is generally co-planar with bottom walls 36 and 76 of immiscible phase well 26 and output well 66, respectively. As best seen in FIG. 2, first and second sidewalls 80 and 82, respectively, of second channel 79 constrict towards each other from input 92 to output 102, for reasons hereinafter described. Upper wall 84 and bottom wall 76 of second channel 79 may also constrict towards each other, for reasons hereinafter described.

In operation, device 10 may be used to isolate weakly interacting molecules from a fluidic sample 106 according to the methods of the present disclosure. With reference to FIGS. 1 and 2, a pathway 2-2 interconnecting the input zone 12 (comprising the mixture of the fluidic sample 106, which comprises target molecules 108, and the solid phase substrate 110 with at least one immobilized molecule 104 thereon) with the output zone 66 (comprising the solution 113) runs through a first constriction 62 that separates the input zone 12 from the immiscible phase zone (i.e., the zone comprising the immiscible phase 109) 26, and through a second constriction 102 that separates the immiscible phase zone 26 from the output zone 66. The surface tension and interfacial energy of the immiscible phase 109 in the immiscible phase cavity 37 of immiscible phase zone 26 at output 62 of first channel 38 prevents the fluidic sample 106 from flowing into the immiscible phase cavity 37 of immiscible phase well 26 through output 62 of first channel 38 and the surface tension of the solution in the output cavity 78 of output well 66 at output 102 of second channel 79 prevents the immiscible phase 109 from flowing into output cavity 78 of output well 66 at output 102 of second channel 79. The fluidic sample 106 is deposited into input well 12, the immiscible phase 109 is deposited into immiscible phase well 26, and the solution 113 is deposited into output well 66. The fluidic sample 106 flows into first channel 38 and the immiscible phase 109 flows into second channel 79. Surface tension and interfacial energy between the immiscible phase 109 and the fluidic sample 106 at output 62 of first channel 38 and between the immiscible phase 109 and the solution 113 at output 102 of second channel 79 prevents flow, mixing, or emulsion formation between the immiscible phase 109 and the fluidic sample 106 and the immiscible phase 109 and the solution 113. The mixture 106 is formed by depositing solid phase substrate 110 having immobilized molecule 104 attached thereto into the fluidic sample which contains the target molecule 108. Solid phase substrate-immobilized molecule-target molecule complexes 112 are formed upon incubation.

The "strength" of the immiscible phase barrier relies upon an interfacial energy between the mixture in the input well and the immiscible phase, which resists deflection or displacement from the microfluidic constriction in order to minimize contact area between the two phases. Reduction of the interfacial energy will result in the formation of a continuous aqueous phase or continuous emulsion connecting the input and output wells resulting in the mixing of the mixture and the solution. Excessively high interfacial energies may be too rigid to allow transfer into the immiscible phase.

The fluidic sample and the solid phase substrate comprising at least one immobilized molecule thereon are added to the input zone of the device and incubated to allow the immobilized molecule to interact with a target molecule in the fluidic sample. The immobilized molecule may be immobilized on the solid phase substrate prior to or after addition of the solid phase substrate to the input zone. For example, in one embodiment, the solid phase substrate may be added to the input zone, and at least one molecule immobilized on the solid phase substrate in the input zone. Following immobilization of the molecule on the solid phase substrate, the fluidic sample may be added to the input zone to form the mixture.

Following incubation, the solid phase substrate-immobilized molecule-target molecule complex is transferred into an immiscible phase in the immiscible phase zone, or may be transferred through the immiscible phase and into a solution in the output zone through the pathway interconnecting the input zone and the output zone. As discussed herein, the solid phase substrate-immobilized molecule-target molecule complex may be transferred into the immiscible phase and/or through the immiscible phase and into the solution by application of an external force to the solid phase substrate.

In one embodiment, a magnetic force is used to transfer the solid phase substrate, as previously described. For example, a magnetic bar may be placed under the input well and used to transfer a magnetically responsive solid phase substrate through the immiscible phase and into the solution in the output zone (e.g., an elution buffer). Target molecules and molecules associated therewith will be transferred along with the magnetically responsive solid phase substrate because of the direct or indirect interaction between the target molecule and the molecule immobilized to the solid phase substrate.

In another embodiment, the solid phase substrate is kept stationary by application of a first external force such as, for example, a magnetic force, and the fluidic sample is forced out of the input zone by application of a second external force such as, for example, a peristaltic pump, a syringe, or other methods known to one skilled in the art. As the fluidic sample is forced out of the input zone, the immiscible phase flows from the immiscible phase zone into the input zone, thus immersing the stationary solid phase substrate-immobilized molecule-target complex in the immiscible phase. The immiscible phase may then be sequentially replaced with the solution from the output zone by following a similar procedure.

In yet another embodiment, the solid phase substrate-immobilized molecule-target complex is kept stationary by application of an external force (e.g., a magnetic or mechanical force) and the device 10 is moved, whereby the stationary solid phase substrate is transferred from the input zone into and through the immiscible phase zone and into the output zone.

In other embodiments centrifugal force is used to transfer the solid phase substrate. For example, an iFAST device can be positioned on a centrifuge rotor in a direction parallel to the centrifugal force. The device would be oriented such that the output zone of the device would be positioned farthest from the center of the rotor and the input zone placed closest to the center of the rotor. A sufficient amount of centrifugal force is needed to direct the particles out of the input zone and into the immiscible phase. The applied force should be less than that causing a disruption of the immiscibility between the mixture in the input zone, the immiscible phase and between the immiscible phase and the solution in the output zone.

Other embodiments may apply mechanical or physical force to a solid phase substrate such as a rod or a wire. For example, a section of a rod or a section of a wire may be pushed from the input end of the device or pulled from the output end of the device in a manner that results in the section of rod or the section of wire being transferred from the input zone into and through the immiscible phase zone and into the output zone.

Another embodiment may use gravitational force to transfer the solid phase substrate from the input zone into and through the immiscible phase zone and into the output zone.

In each of these embodiments, the target molecules and any molecules associated therewith would be transferred along with the solid phase substrate because of the interaction between the target molecule and the immobilized molecule.

Figure 3B:
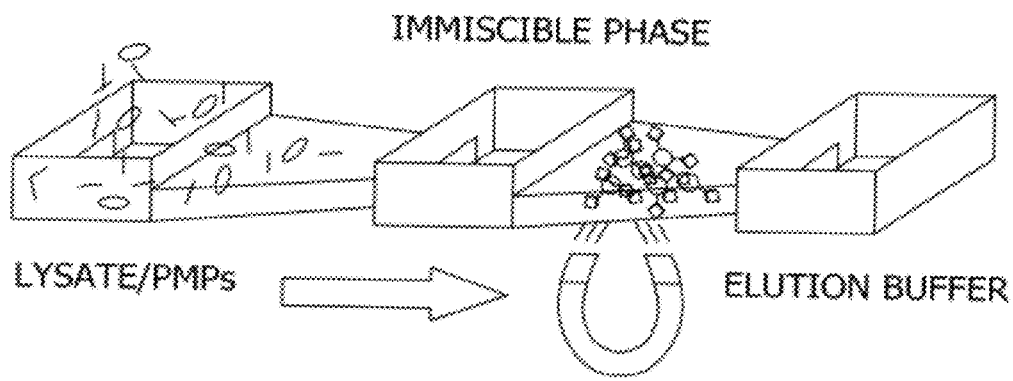
FIG. 3B is an illustration of a three well iFAST device showing the transfer of PMP-immobilized molecule-target molecule complexes through the immiscible phase zone using a magnet.

One particular example of a method of the present disclosure is illustrated in FIG. 3. As shown in FIG. 3, the iFAST device used in this exemplary embodiment has three wells in a linear configuration connected by two trapezoidal microfluidic conduits or channels. A fluidic sample (e.g., a lysate) is deposited in the input well of the iFAST device along with a solid phase substrate (e.g., paramagnetic particles (PMPs)) having at least one molecule immobilized thereon, to form a mixture (see FIG. 3A). An immiscible phase (e.g., a liquid wax or oil) is deposited in the center well, and a solution (e.g., an elution buffer) is deposited in the output well.

In order to isolate molecules that weakly interact with the immobilized ligand, a force to which the solid phase substrate is attracted (e.g., a magnet) is positioned below the input well, such that the solid phase substrate is magnetically attracted thereto. The magnet is sequentially moved 1) below the bottom wall of the first channel, such that a solid phase substrate-immobilized molecule-target molecule complex is drawn into the first channel; 2) below the bottom wall of the center (immiscible phase) zone such that the complex is drawn through the first constriction and into the immiscible phase; 3) below the bottom wall of the second channel, such that the complex is drawn into the second channel (see FIG. 3B); and 4) below the bottom wall of the output zone, such that the complex is drawn into the output zone through the second constriction (see FIG. 3C).

Figure 4:
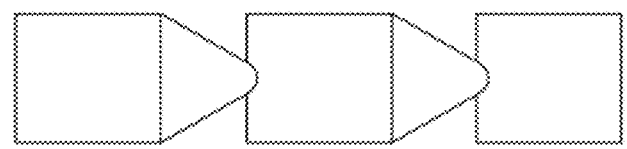
FIG. 4 is a cross-sectional view of a three well iFAST device.
Figure 5:
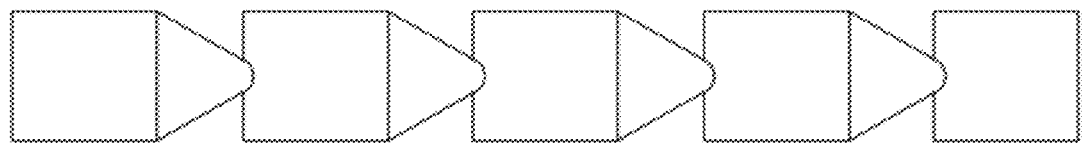
FIG. 5 is a cross-sectional view of a five well iFAST device.

As discussed herein, the methods of the present disclosure optionally may further comprise subjecting the solid phase substrate-immobilized molecule-target molecule complex to an additional filtration by transferring the complex from the solution through a second immiscible phase and into a second solution. FIGS. 4 and 5 compare the set up for an iFAST device suitable for performing a single immiscible phase filtration (see FIG. 4) and the set up for an iFAST device suitable for performing a double immiscible phase filtration (see FIG. 5).

Because the iFAST device uses surface tension-dominant physics associated with the microscale to position aqueous and immiscible phases side by side, the solid phase substrate-immobilized molecule-target molecule complex can be rapidly transferred from the mixture in the input zone through the immiscible phase and into the solution in the output zone. Further, the wash steps used in conventional methods are not required. Not only do the wash steps add significant time to conventional protocols, but weakly interacting molecules may also be rendered undetectable.

Figure 7:
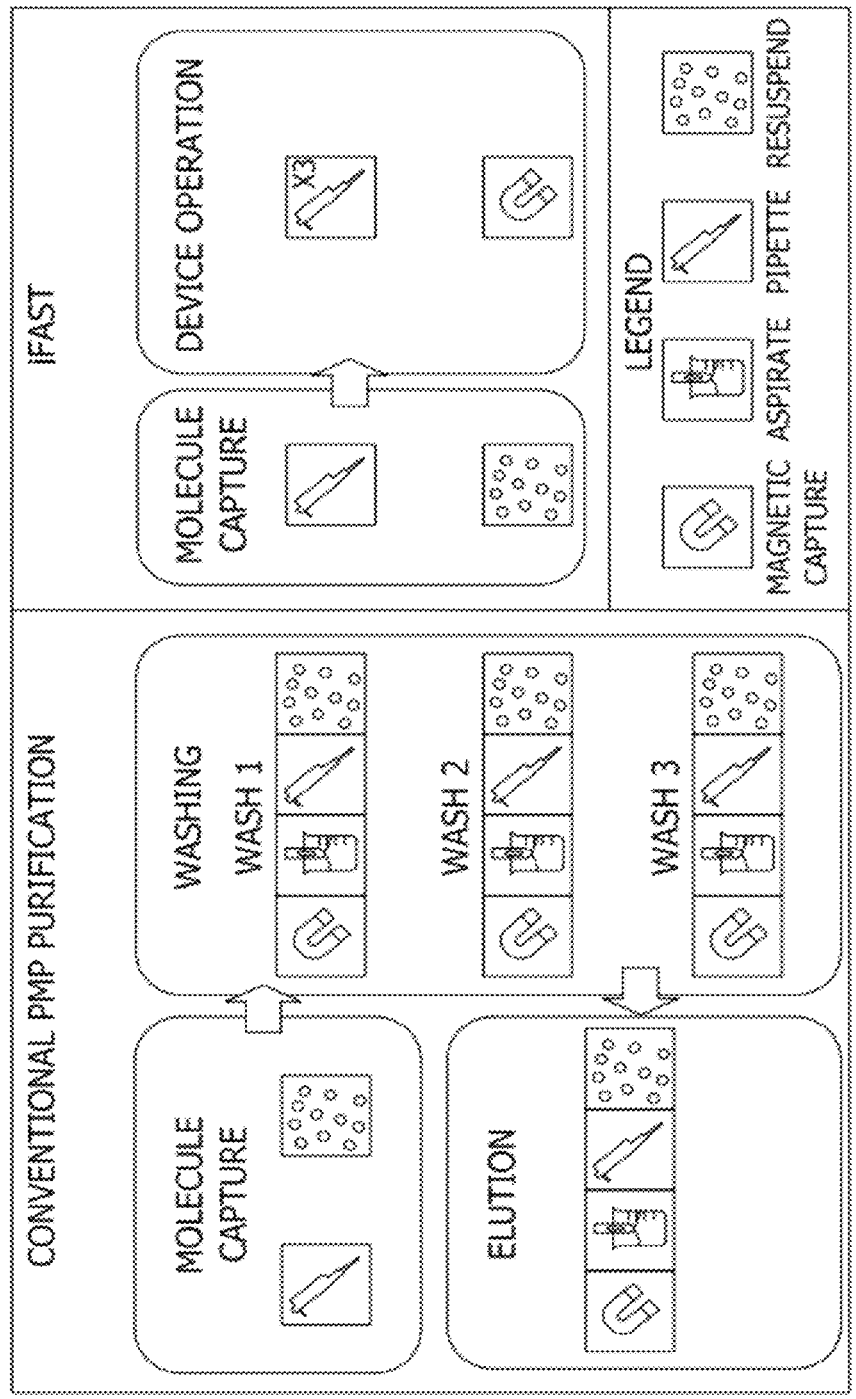
FIG. 7 is an illustration comparing the steps and handling of materials using an immiscible phase filtration technique of the present disclosure with the steps and handling of materials in conventional immunoprecipitation using paramagnetic particles.

FIG. 7 illustrates and compares an exemplary immiscible phase filtration technique of the present disclosure performed using an iFAST device, with paramagnetic particles as the solid phase substrate, with a conventional immunoprecipitation technique performed using paramagnetic particles. Both protocols use a similar first step of pipetting each reagent into a reaction well. In this exemplary embodiment, the immiscible phase filtration technique involves three pipetting steps: 1) pipetting a fluidic sample into the input zone; 2) pipetting an immiscible phase into the immiscible phase zone; and 3) pipetting a solution into the output zone. After incubating the fluidic sample and paramagnetic particles (which have an immobilization ligand thereon) for a sufficient time to allow capture of target molecules, a magnet is placed near the input zone of the iFAST device and reaction vessel of the conventional protocol to aggregate the paramagnetic particles. In the immiscible phase filtration technique, the magnet is used to rapidly transfer the captured complexes into the immiscible phase and/or further into the output zone. In the conventional protocol, a pipette is used to aspirate the mixture including any unbound material. A pipette is then used to transfer the first wash buffer into the reaction vessel for wash 1. The magnetic force may be removed prior to or after the wash buffer is added to the reaction vessel. Typically, the wash buffer is agitated in some manner to enhance resuspension of the particles. For example, agitation may be by pipetting, vortexing, tapping the reaction tube, or other methods know in the art. Typically, the resuspended particles are incubated in the wash buffer for some time period (e.g., 3 to 5 minutes or more). The magnet is again applied to capture the particles in preparation for aspirating the first wash buffer. The washing step is then repeated as described above for three to five times. Thus, each wash step in the conventional protocol involves the application of the magnet, aspiration of the wash buffer, adding new wash buffer, removing the magnetic force, resuspending the particles, and incubation. Following the last wash buffer incubation, the conventional protocol is completed by applying the magnetic force to capture the particles, aspirating the wash buffer, and resuspending the particles as described above in elution buffer or some other downstream processing solution. Thus, the immiscible phase filtration technique involves far less steps than the conventional protocol and significantly reduces the processing time to complete the isolation. The immiscible phase filtration technique also reduces the number of times the particles are manipulation and the number of reagents required.

The disclosure will be more fully understood upon consideration of the following non-limiting Examples.

EXAMPLES iFAST Device

Unless otherwise indicated, the iFAST devices used in the following examples were prepared as described below.

Microfluidic iFAST devices were fabricated from polydimethylsiloxane (PDMS) using soft lithography, and then bound to glass bottoms using oxygen plasma to enhance bond strength. As depicted in FIG. 3, iFAST devices were fabricated with three wells (Volume=10 µl) connected by two trapezoidal microfluidic channels (or pathways). As depicted in FIG. 5, iFAST devices were also fabricated with five wells. The shape of the microfluidic conduit was selected to establish a region of minimal surface energy, termed a "virtual wall". (See, Atencia and Beebe, Nature 437:648-655 (2005); Zhao et al., Science 291:1023-1026 (2001)). During device filling, liquid flowed from the well area into the microchannel pathway, but stopped at the narrowest part of the microchannel pathway rather than going into the next well due to the consequent increase in surface energy at the area of constriction. This phenomenon enabled the serial filling of the interconnected wells since each liquid was sequestered within its own region by virtual walls.

Example 1

In this Example, a three well iFAST device was used to isolate molecules from a cell lysate using paramagnetic particles as the solid phase support and antibodies as the immobilized molecule.

Specifically, a solution containing 7.5 mg/ml Protein G-conjugated PMPs (Dynabeads Protein G, Invitrogen) and 0.031 mg/ml anti-GFP epitope monoclonal antibody (mAb) in 0.01% Tween 20/phosphate buffered saline (PBS) was prepared and incubated for 30 minutes at room temperature to allow mAb attachment to the PMPs. Following washing with 0.01% Tween 20/PBS, mAb-labeled PMPs were re-suspended in PBS (15 mg/ml PMP concentration) and 2% (by volume) bacterial lysate was added. Bacterial lysate was prepared from $E.\ coli$ lysate that was adjusted to 300 mM NaCl and then supplemented with polyethyleneimine to a final concentration of 0.3% to precipitate RNA polymerase (epitope tag source) and the nucleic acids, which were removed by centrifugation. Following a 10-minute incubation at room temperature with rotation, the solution was loaded into the three well iFAST device and purified.

Figure 3C:
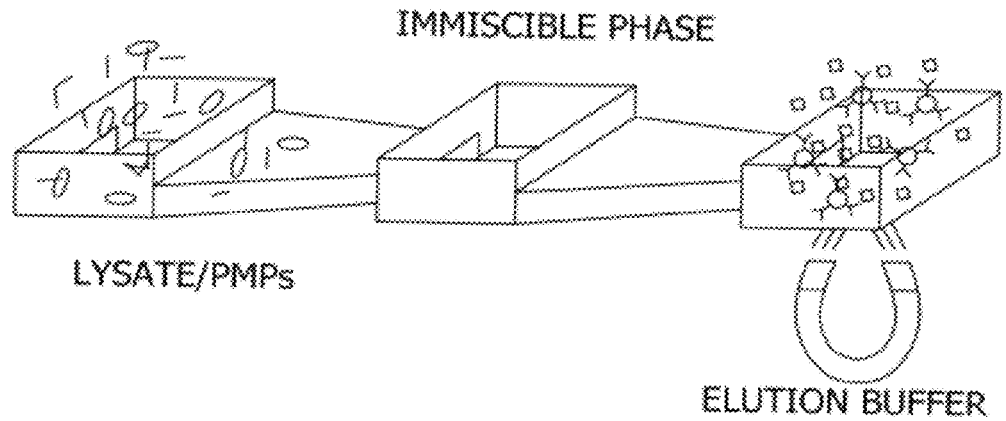
FIG. 3C is an illustration of a three well iFAST device showing PMP-immobilized molecule-target molecule complexes in the elution buffer in the output zone.

Antibody-labeled paramagnetic microparticles ("PMPs") were mixed with cell lysate and allowed to bind with the target-of-interest. After binding, 8.5 µl of lysate, 8.5 µl of immiscible phase (Chill-Out Liquid Wax, Bio-Rad, or olive oil, Unilever), and 8.5 µl elution buffer (50 mM Tris-HCl and 0.1 mM EDTA (pH 7.9) containing 750 mM ammonium sulfate (AS) and 40% propylene glycol) were added to the input well, the immiscible phase well, and the output well, respectively, (see FIG. 3A-B) using a pipette or other liquid handler. A magnetic bar (K&J Magnetics) was then placed under the input well and used to transfer the PMP aggregate through the immiscible phase and into elution buffer at a rate of approximately 2 mm/sec (total traverse time≈10 sec) (FIG. 3C). Once in the elution buffer, PMPs were given 2 minutes for elution before the eluate was collected using a pipette for analysis.

Alternately, purification was performed using conventional PMP-based purification following manufacturer's protocol (Invitrogen Immunoprecipitation Kit—Dynabeads Protein G). Briefly, the manufacturer's protocol used a magnetic stand (DynaMag-2, Invitrogen) to aggregate PMPs from 100 μl of PMP/lysate solution on the side of a 1.5 ml microcentrifuge tube. After removing the supernatant, 200 μl of Wash Buffer (Invitrogen IP kit) was added and the PMP aggregate was resuspended by agitation with a micropipette. The wash process was repeated for a total of three washes before the protein was eluted in the previously-mentioned elution buffer.

Figure 8:
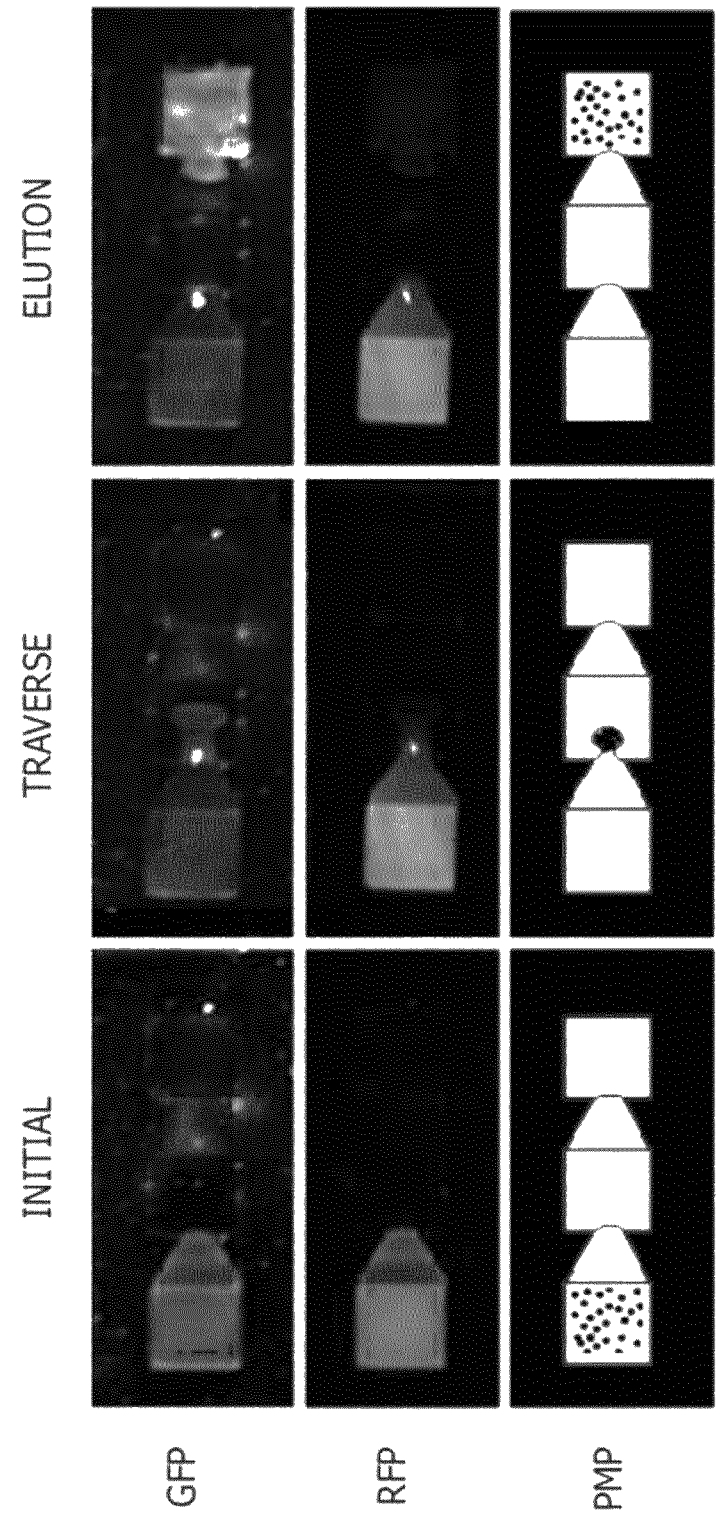
FIG. 8 depicts the transfer of green fluorescent protein (GFP) using an iFAST device from a bacterial lysate containing a mixture of GFP and red fluorescent protein (RFP) in the initial input well and into the elution solution, as discussed in Example 1.

Representative iFAST samples were fluorescently imaged during purification (Fotodyne Luminary). As depicted in FIG. 8, GFP in the bacterial lysate interacted with anti-GFP epitope monoclonal antibody immobilized to PMP and was transferred from the lysate well (Initial) through the immiscible phase (Traverse) and into the elution well (Elution). Unbound RFP remained in the lysate well (Initial). The bottom panel of FIG. 8 depicts the position of PMP-antibody-GFP complexes during each step in the iFAST process.

Figure 9:
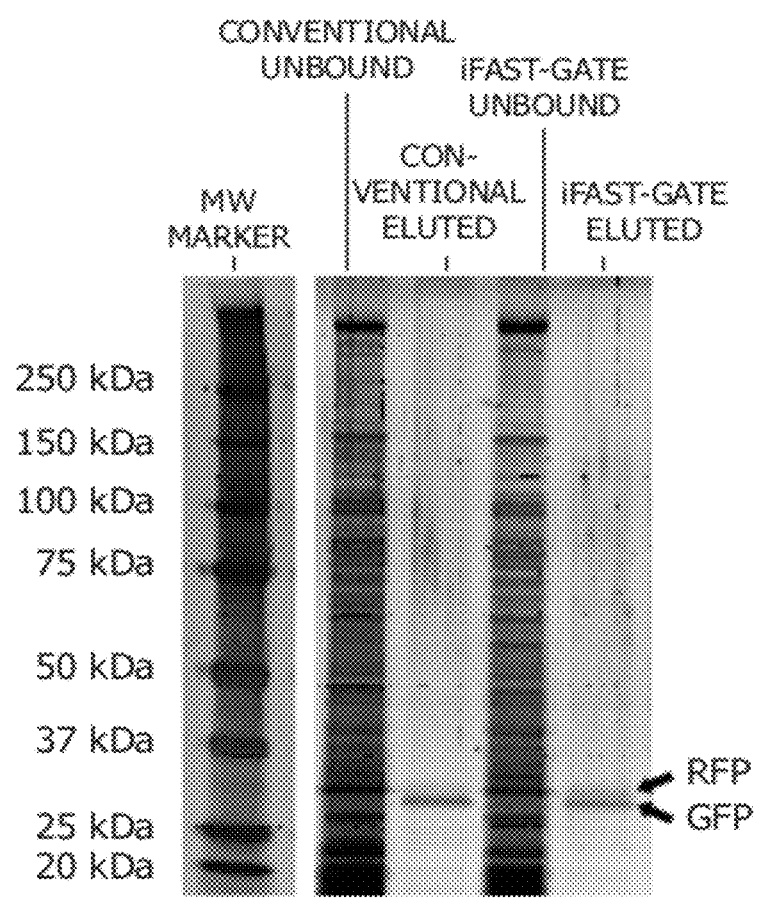
FIG. 9 depicts isolation of GFP from a bacterial lysate containing a mixture of GFP and RFP using an immiscible phase filtration technique, as analyzed by SDS-PAGE followed by silver staining, as discussed in Example 1.
Figure 10:
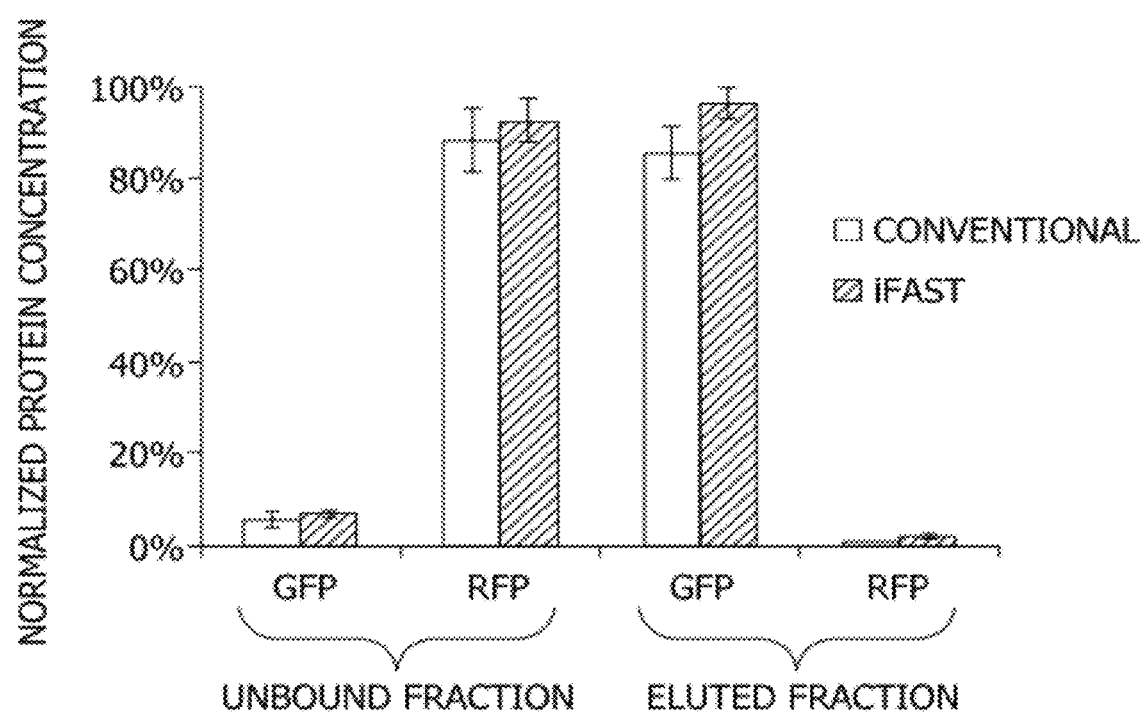
FIG. 10 is a graph depicting recovery of GFP following iFAST compared to conventional immunoprecipitation, as discussed in Example 1.

Following elution at room temperature for 2 minutes in elution buffer (50 mM Tris-HCl and 0.1 mM EDTA (pH 7.9) containing 750 mM ammonium sulfate (AS)), purified proteins were collected and analyzed for GFP and RFP content. Specifically, eluates were loaded into 1536-well plates and imaged using a fluorescent scanner (Typhoon Trio, GE) and quantified with ImageQuant software. Some eluates were loaded into SDS-PAGE gels (NuPAGE 4-12% Bis-Tris Gel, Invitrogen), electrophoretically separated for 50 minutes at 200 V, and imaged using silver stain (SilverQuest Silver Staining Kit, Invitrogen). As depicted by SDS-PAGE in FIG. 9, the isolation of GFP from bacterial lysate by using the iFAST device was comparable to the protein content of eluted and uncaptured material using the conventional PMP-based assay. As further depicted in FIG. 10, the majority (~96%) of GFP was recovered following iFAST traverse while the majority (~93%) of RFP remained in the input (Initial) well (labeled as "Unbound Fraction").

Example 2

In this Example, an iFAST device was used to demonstrate the isolation of weakly interacting molecules.

It has been demonstrated that the strength of the mAb/epitope tag interaction can be weakened by increasing ammonium sulfate (AS) concentration, such that weakly bound complexes can be artificially generated in a predictable and repeatable manner. To demonstrate the ability of the methods and devices of the present disclosure to isolate weak protein-protein interactions, lysate containing epitope-tagged GFP protein (1% by volume, approximately 12 μg/ml GFP) was mixed with mAb-labeled PMPs in a variety of solutions containing 20% propylene glycol and 0 to 250 mM AS and incubated for 30 minutes at room temperature to allow protein binding. iFAST of GFP was compared to washing-based protocols as described in the previous Example, except that the washing and binding solutions were replaced by AS buffers (50 mM Tris-HCl and 0.1 mM EDTA (pH 7.9) containing 0 to 250 mM AS and 20% propylene glycol). Elution was performed as described above in a solution containing 750 mM AS and 40% propylene glycol. GFP recovered was quantified using a fluorescent scanner.

When increasing concentrations of AS were added to the binding and washing buffers, it was found that use of the iFAST device resulted in recovery of significantly more GFP, particularly for AS concentrations ranging from 1 to 30 mM. Within that regime, complex dissociation during washing (total time≈10 minutes) was substantial and large quantities of protein were lost in the wash buffer of the conventional assay. For AS concentration in excess of 30 mM, initial complex formation was unfavorable and the vast majority of GFP remained unbound following the 30 minute incubation with mAb-labeled PMPs, although significantly more GFP was recovered with using the iFAST device (p<0.005). For low AS concentration (1 mM range), complex dissociation was slow and the majority of GFP was recovered with both techniques.

Table 1 summarizes data for each concentration. These data suggest that the methods and devices of the present disclosure can recover more protein relative to conventional wash-based protocols when the interaction with the solid phase (i.e., PMPs) is weak, such that a significant quantity of protein is inadvertently dissociated during the wash steps of the conventional assay. Surprisingly, data demonstrated a 40× increase in the amount of weakly interacting molecules captured. "Unbound" material refers to GFP that is not bound to the PMP/mAb resin following binding incubation. Note that for high AS concentration (weak mAb-GFP interaction) most of the GFP remained in the unbound fraction, while for low AS concentration (strong mAb-GFP interaction) most of the GFP was successfully collected in the elution fraction. For intermediate concentrations of AS, the majority of the GFP was lost during washing when using the conventional protocol, but recovered when using iFAST. The ratio of GFP eluted when using the iFAST to GFP eluted with the conventional washing method is provided in the rightmost column. Values were the average of 4 determinations.

TABLE 1

Distribution of GFP following Conventional and iFAST methods.

| AS Concentration (mM) | Conventional | | | iFAST | | Elution Fold Increase |
|---|---|---|---|---|---|---|
| | Unbound | Eluted | Washes | Unbound | Eluted | |
| 0 | 1% | 54% | 44% | 5% | 95% | 1.7 |
| 0.5 | 5% | 53% | 43% | 6% | 94% | 1.8 |
| 1.0 | 9% | 63% | 28% | 10% | 90% | 1.4 |
| 2 | 5% | 43% | 52% | 19% | 81% | 1.9 |
| 4 | 6% | 20% | 74% | 5% | 95% | 4.7 |
| 8 | 17% | 14% | 70% | 33% | 67% | 5.0 |
| 15 | 26% | 6% | 68% | 58% | 42% | 7.4 |
| 30 | 45% | 2% | 53% | 76% | 24% | 10.0 |
| 60 | 61% | 0.4% | 38% | 90% | 10% | 28.3 |
| 120 | 61% | 0.3% | 38% | 90% | 10% | 34.7 |
| 250 | 70% | 0.2% | 30% | 90% | 10% | 43.7 |

These results demonstrate that the methods and devices of the present disclosure represent a new and efficient method for isolating weakly interacting molecules.

Example 3

In this Example, weakly interacting complexes containing the NEMO protein were isolated using immiscible phase filtration and an iFAST device.

Although NEMO is thought to complex with many proteins, four specific target proteins were of interest in this Example. Two of these target proteins, IKKα and IKKβ, are known to form strong complexes with NEMO, while two other target proteins, PiaSY and SenP2, are thought to form relatively weak complexes. Each of these target proteins was tagged with an epitope (FLAG) to aid in quantification, and NEMO protein was tagged with a Myc epitope. Anti-FLAG antibodies were immobilized on Protein G-coated paramagnetic particles (PMPs). The PMPs with immobilized anti-FLAG antibody were then incubated for 30 minutes or overnight with lysate in order to capture NEMO and any associated proteins. The PMP-anti-FLAG solid phase substrate and any interacting NEMO complexes were isolated using either an immiscible phase filtration technique of the present disclosure or processed according to conventional immunoprecipitation using five washes with IP buffer containing detergent (20 mM Tris Chloride pH 7.5, 250 mM NaCl, 3 mM EDTA, 3 mM EGTA, 0.5% NP-40). The immiscible phase filtration and conventional immunoprecipitation techniques were also performed using protein G-coated PMPs having anti-Myc antibodies immobilized thereon in order to capture Myc-tagged NEMO and any additional NEMO-interacting molecules (specifically IKKα, IKKβ, PiaSY and SenP2). Table 2 summarizes the potential combinations of solid phase substrate, immobilized molecule, target molecule, and at least one additional molecule.

TABLE 2

Combination of solid phase substrate, immobilized molecule, target molecule, and at least one additional molecule.

| Solid Phase Substrate | Immobilized Molecule | Target Molecule | Additional Molecule |
|---|---|---|---|
| PMP | Anti-FLAG Antibody | IKKα (FLAG tagged) | NEMO (Myc tagged) |
| PMP | Anti-FLAG Antibody | IKKβ (FLAG tagged) | NEMO (Myc tagged) |
| PMP | Anti-FLAG Antibody | PiaSY (FLAG tagged) | NEMO (Myc tagged) |
| PMP | Anti-FLAG Antibody | SenP2 (FLAG tagged) | NEMO (Myc tagged) |
| PMP | Anti-Myc Antibody | NEMO (Myc tagged) | IKKα (FLAG tagged) |
| PMP | Anti-Myc Antibody | NEMO (Myc tagged) | IKKβ (FLAG tagged) |
| PMP | Anti-Myc Antibody | NEMO (Myc tagged) | PiaSY (FLAG tagged) |
| PMP | Anti-Myc Antibody | NEMO (Myc tagged) | SenP2 (FLAG tagged) |

A modified iFAST device was used to perform the immiscible phase filtration. Specifically, an iFAST device having an input well that would hold a volume of 200 μl was configured. The immiscible phase well and the output well were configured to hold 8.5 μl. This configuration allowed for isolation from an input volume of 200 μl into an output volume of 8.5 μl, thus concentrating the sample ~24 fold. This configuration was implemented to increase the total volume of input lysate in order to increase the total amount of protein, since much of the weakly-bound target protein was expected to exist in the non-complexed state, thus lowering the maximum total recovery (i.e. non-complexed protein will not attach to the PMP). To ensure a proper comparison, the input and output volumes of the immiscible phase filtration and washing protocols were kept equal.

Following isolation of the PMPs, target proteins and any molecules interacting therewith were eluted from the PMPs by resuspending the PMPs in SDS-sample buffer, and subjected to Western blot analysis. Western blots were probed using an anti-Myc antibody.

Figure 11:
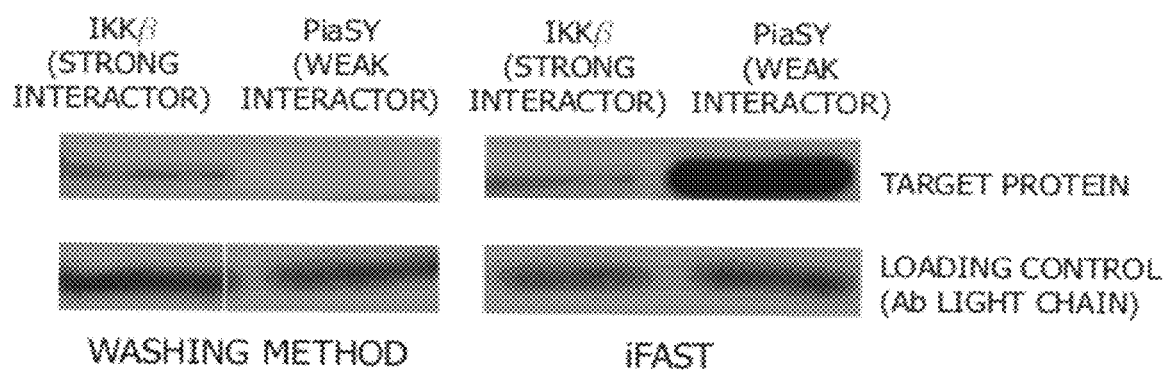
FIG. 11 is a Western blot showing the isolation of NEMO using IKKβ target complexes, and PiaSY target complexes using an immiscible phase filtration technique of the present disclosure as compared to conventional immunoprecipitation, as discussed in Example 3.
Figure 12:
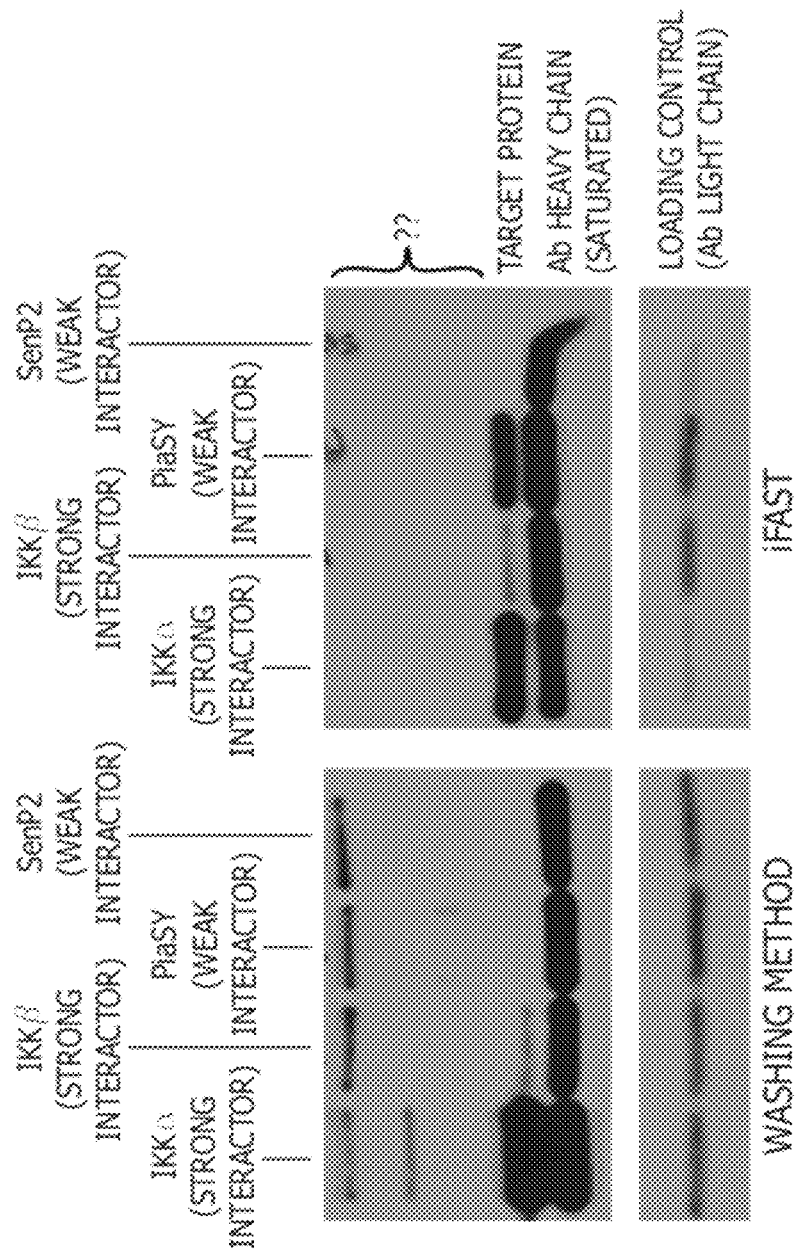
FIG. 12 is a Western blot showing the isolation of NEMO using IKKα target complexes, IKKβ target complexes, and PiaSY target complexes using an immiscible phase filtration technique of the present disclosure as compared to conventional immunoprecipitation, as discussed in Example 3.

As can be seen in FIGS. 11 and 12, NEMO was captured through strong interactions with immobilized IKKα and immobilized IKKβ using the immiscible phase filtration method and conventional immunoprecipitation. Significantly, the immiscible phase filtration method also isolated one of the known weak interactions. In particular, NEMO was captured by immobilized PiaSy protein. In contrast, conventional immunoprecipitation failed to isolate NEMO using either weakly interacting protein (i.e., PaiSY and SenP2). Since both the immobilized anti-FLAG antibody and the primary antibody used in the Western blot were from the same species, the immobilized anti-FLAG antibody, which separates into its heavy and light chains during SDS-PAGE, was detected in the Western blot analysis. Detection of the immobilized antibody served as a "PMP recovery control" because the level of this antibody should be proportional to the quantity of PMPs collected at the elution side of the method.

Example 4

In this Example, nucleic acid-nucleic acid interactions were isolated using the methods and devices of the present disclosure.

Specifically, breast cancer epithelial cells (MCF-7) were cultured in Dulbecco's Modified Eagle Medium (DMEM) at 37° C. in polystyrene flasks until confluence. Cells were released using a 0.05% trypsin/EDTA solution and collected via centrifugation. Cell pellets were frozen at −80° C. until nucleic acid (NA) isolation procedures were performed.

Cell pellets were mixed with a solution containing 0.7 mg/ml oligo-dT PMPs (from Dynabeads mRNA Direct Kit, Invitrogen) in lysis buffer (1% LiDS, 100 mM Tris-HCl, 500 mM LiCl, 10 mM EDTA, 5 mM DTT) and incubated for five minutes at room temperature to allow lysis and binding. For the iFAST devices based on 384-well plate architecture, 8.5 μl of the lysate/PMP mixture and elution buffer (10 mM Tris-HCl) were added to the input and output wells, respectively. These solutions immediately filled their individual compartment, but resisted filling through the microfluidic constrictions (virtual walls). Next 8.5 μl of oil was added to the middle well, filling the remaining device area between the input and output wells. For iFAST devices based on the 1536-well plate architecture, volumes were reduced to 3 μl.

The filled devices, which were operated in arrays of five, were placed on top of a magnet (K&J Magnetics B333, N52-grade neodymium cube (0.64 T) for single iFAST operation; BX041, N52-grade neodymium bar (1.48 T) for arrayed iFAST operation), aligning the input well with the magnet surface. Magnets that were wider than the iFAST device(s) were chosen such that the magnetic field was distributed relatively uniformly across device (i.e., no edge effects), causing the PMPs to be pulled against the glass device bottom in a uniform line spanning the width of the device, thus preventing coagulation at maxima in the magnetic field. The magnet was moved at a velocity of ~5 mm/s, drawing the PMPs across the oil barrier and into the elution buffer. The eluent was collected via pipette for RT-PCR.

Conventional Nucleic Acid Purification

Commercial NA isolation kits were run in parallel with the iFAST device. Cell pellets were re-suspended and split into aliquots containing equal cell numbers, which were then purified using either silica membrane spin column-based (Qiagen RNeasy) or PMP-based (Ambion MagMAX) NA isolation kits as per the manufacturers protocol. In the case of the silica membrane kit, a homogenizer (Qiagen QiaShredder) was used to pre-process the cultured cells as per the manufacturer's recommendation.

RT-PCR

Isolated mRNA was reverse transcribed using a cDNA synthesis kit (iScript cDNA Synthesis Kit, Bio-Rad) at 42° C. for 30 minutes followed by 85° C. for 5 minutes. This cDNA was then mixed with qPCR master mix (SYBR® Green PCR Master Mix, Bio-Rad) and amplified for 40 cycles (95° C. for 15 seconds, then 57 to 60° C. for 1 minute) using a thermal cycler (MyiQ Thermal Cycler, Bio-Rad). Primers spanned introns such that gDNA contamination could be identified from an analysis of a post-amplification melt curve. Gene expression levels were quantified by determining the CT at which exponential amplification was observed. Standard curves of PCR amplification efficiency were generated by preparing five serial dilutions of cDNA, plotting these values against CT, then using the slope of this plot to calculate efficiency.

iFAST Performance

Figure 13:
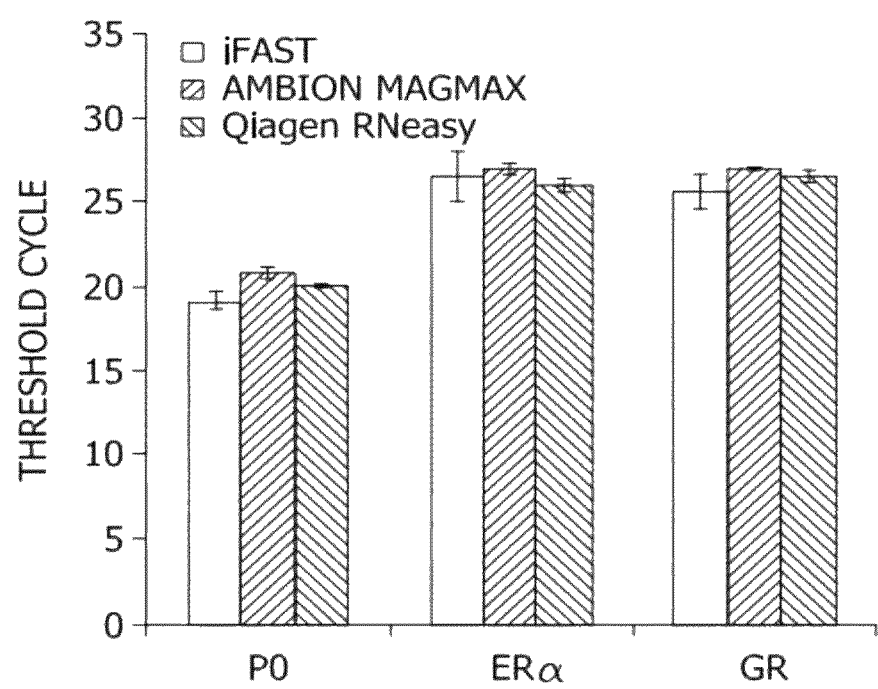
FIG. 13 is a graphical illustration comparing cycle threshold values of three nucleic acids isolated by the method of the present disclosure compared to two commercially available techniques, as discussed in Example 4.

The performance of the iFAST platform was quantified using four metrics commonly applied to nucleic acid purification: 1) Amplification efficiency of a downstream qRT-PCR reaction, 2) Nucleic acid yield, 3) Scalability to small sample sizes, such as those associated with biopsied tumors, cheek swabs, and forensic samples, and 4) Overall time to complete the process. Amplification efficiencies of sample prepared using the iFAST platform were found to be between 90% and 110% for multiple genes, indicating that the nucleic acids have been sufficiently separated from the PCR interferents present in whole cell lysate as presence of significant carry-over lysate would impede amplification and reduce efficiency. Nucleic acid yield was assessed through a direct comparison between the iFAST platform and popular commercially-available kits (Qiagen RNeasy Mini Kit and Ambion MagMAX Kit), in which samples containing ~56,000 cells were processed by each technique and multiple genes were amplified and detected via qRT-PCR. Comparison of cycle threshold (CT) values of large ribosomal protein (P0), and two low abundance genes, estrogen receptor-$\alpha$ (ER$\alpha$) and glucocorticoid receptor (GR), in lysates from cancer cells prepared via iFAST, silica membrane-based commercial kits, or PMP-based commercial kits indicated that that NA yield was comparable to or better than the commercial kits (see FIG. 13).

Example 5

In this Example, the extent of mRNA loss when using the methods and devices of the present disclosure was determined.

The recovery of pure mRNA was quantified as it was transferred across the iFAST device. Briefly, mRNA was purified from lysate via iFAST using PMP as the solid phase substrate, and this mRNA was either directly amplified or processed a second time with the iFAST device and then amplified. It was found that the CT values for P0 amplified from these two samples were within 0.2 cycles of each other (p=0.82 by paired t-test, n=3), suggesting that virtually no mRNA was lost during PMP binding, immiscible phase traverse, and elution. Furthermore, mRNA was effectively isolated from genomic DNA (gDNA) using oligo-dT-bound PMPs (Invitrogen oligo-dT Dynabeads) that selectively capture the poly-A tails of mRNA. Using these PMPs, the ratio of RNA to gDNA for the P0 gene was found to be ~130,000:1 as measured by no-RT controls. Additionally, the post-amplification melt curve from NA isolated with the oligo-dT PMPs contained no noticeable gDNA contamination. This is in contrast to silica PMPs (Ambion MagMAX) that capture total NA and generated an RNA to gDNA ratio of ~1,000:1 for the same gene. The scalability of the iFAST platform was evaluated by preparing a variety of sample sizes ranging from 1 to 65,000 cells and amplifying multiple genes after iFAST purification. Minimal sample loss was observed as the device was scaled down as indicated by the similarity of the experimental data with the theoretical amplification time when complete scalability is assumed (i.e. reducing sample size by a factor of 2 will require 1 more cycle to achieve detection). Significantly, total time-to-preparation was reduced by >75% over both commercial kits tested.

These results demonstrated that the methods and devices of the present disclosure can be used to isolate nucleic acid molecules by nucleic acid-nucleic acid interactions. Because of the speed in which the methods can be performed, it is contemplated that the methods may be useful for isolating weakly interacting nucleic acid-nucleic acid complexes.

What is claimed is:

1. A method for isolating weakly interacting molecules from a fluidic sample, the method comprising:
   a) forming a mixture comprising the fluidic sample and a solid phase substrate, wherein the solid phase substrate comprises at least one immobilized molecule thereon;
   b) incubating the mixture under conditions sufficient for the immobilized molecule to interact with a target molecule in the fluidic sample to form a solid phase substrate immobilized molecule-target molecule complex, wherein the immobilized molecule and the target molecule have an interaction half-life of about 10 minutes or less; and
   c) transferring the solid phase substrate-immobilized molecule-target molecule complex into an immiscible phase in about 1 second or less;
   wherein the forming and the incubating are performed in an input zone of a device comprising:
   i) the input zone; and
   ii) a zone comprising the immiscible phase;
   wherein a first constriction separates the input zone from the zone comprising the immiscible phase.

2. The method of claim 1, wherein the solid phase substrate immobilized molecule-target molecule complex is transferred into the immiscible phase in about 10 milliseconds or less.

3. The method of claim 1, wherein the immobilized molecule and the target molecule have an interaction half-life of about 2 seconds or less.

4. The method of claim 1, further comprising transferring the solid phase substrate-immobilized molecule-target molecule complex through the immiscible phase and into a solution.

5. The method of claim 4, wherein the solid phase substrate-immobilized molecule-target molecule complex is transferred from the mixture, through the immiscible phase, and into the solution in about 10 seconds or less.

6. The method of claim 4, wherein the solution is selected from the group consisting of an elution buffer, a downstream process reagent, a detection reagent, and combinations thereof.

7. The method of claim 4, further comprising transferring the complex from the solution through a second immiscible phase and into a second solution.

8. The method of claim 4, further comprising forming and incubating the mixture in an input zone of a device comprising:
  i) an output zone comprising the solution, wherein the mixture in the input zone and the solution in the output zone are separated by the zone comprising the immiscible phase; and
  ii) a pathway interconnecting the input zone and the output zone, wherein the first constriction separates the input zone from the zone comprising the immiscible phase and a second constriction separates the zone comprising the immiscible phase from the output zone; and
  wherein the solid phase substrate-immobilized molecule-target molecule complex is transferred from the mixture in the input zone through the pathway through the zone comprising the immiscible phase and into the solution in the output zone.

9. The method of claim 1, wherein the immobilized molecule-target molecule interaction is selected from the group consisting of a protein-protein interaction, a nucleic acid-nucleic acid interaction, a protein-protein complex interaction, a protein-small molecule interaction, a nucleic acid-small molecule interaction, a small molecule-small molecule interaction, a cell-protein interaction, a cell-nucleic acid interaction, a cell-small molecule interaction, a cell-protein complex interaction, and combinations thereof.

10. The method of claim 1, wherein the immobilized molecule is selected from the group consisting of a protein, nucleic acid, a small molecule, a cell, and combinations thereof.

11. The method of claim 1, wherein the target molecule is selected from the group consisting of a protein, a protein complexed with at least one additional molecule, a nucleic acid, a nucleic acid complexed with at least one additional molecule, a small molecule, a small molecule complexed with at least one additional molecule, a cell, a cell complexed with at least one additional molecule, and combinations thereof.

12. The method of claim 1, wherein the solid phase substrate is responsive to an external force.

13. The method of claim 12, wherein the external force is selected from the group consisting of a magnetic field, air, gravitational force, centrifugal force, inertial force, mechanical force, pumping, and combinations thereof.

14. The method of claim 1, wherein the solid phase substrate is selected from the group consisting of a non-magnetic particle, a paramagnetic particle, a superparamagnetic particle, a magnetic particle, a ferromagnetic particle, a porous particle, a non-porous particle, a membrane, a rod, a wire, and combinations thereof.

15. The method of claim 1, wherein the immiscible phase is selected from the group consisting of an organic solvent, a liquid wax, an oil, a gas, and combinations thereof.

16. A method for isolating weakly interacting molecules from a fluidic sample, the method comprising:
  a) forming a mixture comprising the fluidic sample and a solid phase substrate, wherein the solid phase substrate comprises at least one immobilized molecule thereon;
  b) incubating the mixture under conditions sufficient for the immobilized molecule to interact with a target molecule in the fluidic sample to form a solid phase substrate immobilized molecule-target molecule complex, wherein the immobilized molecule and the target molecule have an interaction half-life of about 5 seconds or less; and
  c) transferring the solid phase substrate-immobilized molecule-target molecule complex into an immiscible phase;
  wherein the forming and the incubating are performed in an input zone of a device comprising:
  i) the input zone; and
  ii) a zone comprising the immiscible phase;
  wherein a first constriction separates the input zone from the zone comprising the immiscible phase.

17. The method of claim 16, wherein the immobilized molecule and the target molecule have an interaction half-life of about 2 seconds or less.

18. The method of claim 16, wherein the solid phase substrate immobilized molecule-target molecule complex is transferred into the immiscible phase in about 1 second or less.

19. The method of claim 16, further comprising transferring the solid phase substrate-immobilized molecule-target molecule complex through the immiscible phase and into a solution.

20. The method of claim 19, wherein the solid phase substrate immobilized molecule-target molecule complex is transferred from the mixture, through the immiscible phase, and into the solution in about 10 seconds or less.

21. The method of claim 19, wherein an interfacial energy between the mixture and the immiscible phase and the immiscible phase and the solution is from about 0.2 mN/m to about 30 mN/m.

22. The method of claim 19, wherein the solution is selected from the group consisting of an elution buffer, a downstream process reagent, a detection reagent, and combinations thereof.

23. A method for isolating weakly interacting molecules from a fluidic sample, the method comprising:
  a) forming a mixture comprising the fluidic sample and a solid phase substrate, wherein the solid phase substrate comprises at least one immobilized molecule thereon;
  b) incubating the mixture under conditions sufficient for the immobilized molecule to interact with a target molecule in the fluidic sample to form a solid phase substrate immobilized molecule-target molecule complex, wherein the target molecule interacts with at least one additional molecule in the fluidic sample, and wherein the target molecule and the at least one additional molecule have an interaction half-life of about 10 minutes or less; and
  c) transferring the solid phase substrate-immobilized molecule-target molecule complex into an immiscible phase in about 1 second or less;
  wherein the forming and the incubating are performed in an input zone of a device comprising:
  i) the input zone; and
  ii) a zone comprising the immiscible phase;
  wherein a first constriction separates the input zone from the zone comprising the immiscible phase.

24. A method for isolating weakly interacting molecules from a fluidic sample, the method comprising:
  a) forming a mixture comprising the fluidic sample and a solid phase substrate, wherein the solid phase substrate comprises at least one immobilized molecule thereon;
  b) incubating the mixture under conditions sufficient for the immobilized molecule to interact with a target molecule in the fluidic sample to form a solid phase substrate immobilized molecule-target molecule complex, wherein the target molecule interacts with at least one additional molecule in the fluidic sample, and wherein the target molecule and the at least one additional molecule have an interaction half-life of about 5 seconds or less; and c) transferring the solid phase substrate-immobilized molecule-target molecule complex into an immiscible phase, wherein the forming and the incubating are performed in an input zone of a device comprising:
i) the input zone; and
ii) a zone comprising the immiscible phase;
wherein a first constriction separates the input zone from the zone comprising the immiscible phase.

25. A method for isolating weakly interacting molecules from a fluidic sample, the method comprising:
a) forming a mixture comprising the fluidic sample and a solid phase substrate, wherein the solid phase substrate comprises at least one immobilized molecule thereon;

b) incubating the mixture under conditions sufficient for the immobilized molecule to interact with a target molecule in the fluidic sample to form a solid phase substrate immobilized molecule-target molecule complex, wherein the immobilized molecule and the target molecule have an interaction half-life of about 10 minutes or less; and c) transferring the solid phase substrate-immobilized molecule-target molecule complex into an immiscible phase in about 1 second or less;

wherein the forming and the incubating are performed in an input zone of a device comprising:
i) the input zone; and
ii) a zone comprising the immiscible phase;
wherein a first constriction separates the input zone from the zone comprising the immiscible phase.

* * * * *